(12) United States Patent
Zijp et al.

(10) Patent No.: US 10,185,224 B2
(45) Date of Patent: Jan. 22, 2019

(54) METHOD AND APPARATUS FOR INSPECTION AND METROLOGY

(71) Applicant: ASML Netherlands B.V., Veldhoven (NL)

(72) Inventors: Ferry Zijp, Nuenen (NL); Duygu Akbulut, Eindhoven (NL); Peter Danny Van Voorst, Nijmegen (NL); Jeroen Johan Maarten Van De Wijdeven, Eindhoven (NL); Koos Van Berkel, Waalre (NL)

(73) Assignee: ASML Netherlands B.V., Veldhoven (NL)

( * ) Notice: Subject to any disclaimer, the term of this patent is extended or adjusted under 35 U.S.C. 154(b) by 0 days.

(21) Appl. No.: 15/569,086

(22) PCT Filed: Apr. 19, 2016

(86) PCT No.: PCT/EP2016/058640
§ 371 (c)(1),
(2) Date: Oct. 24, 2017

(87) PCT Pub. No.: WO2016/177568
PCT Pub. Date: Nov. 10, 2016

(65) Prior Publication Data
US 2018/0120714 A1 May 3, 2018

(30) Foreign Application Priority Data

May 4, 2015 (EP) .................................... 15166233

(51) Int. Cl.
*G03B 27/52* (2006.01)
*G03B 27/72* (2006.01)
(Continued)

(52) U.S. Cl.
CPC .......... *G03F 7/70641* (2013.01); *G01B 11/14* (2013.01); *G01N 21/956* (2013.01);
(Continued)

(58) Field of Classification Search
CPC .... G01B 11/14; G02B 21/0016; G02B 21/33; G02B 5/3025; G03F 7/70591;
(Continued)

(56) References Cited

U.S. PATENT DOCUMENTS

| 5,946,282 A | * | 8/1999 | Hirono | .................... | B82Y 10/00 |
| | | | | | 369/112.02 |
| 7,791,732 B2 | | 9/2010 | Den Boef et al. | | |

(Continued)

OTHER PUBLICATIONS

International Search Report and Written Opinion dated Sep. 9, 2016 in corresponding International Patent Application No. PCT/EP2016/058640.

(Continued)

*Primary Examiner* — Christina A Riddle
(74) *Attorney, Agent, or Firm* — Pillsbury Winthrop Shaw Pittman LLP

(57) ABSTRACT

A method involving providing incident radiation of a first polarization state by an optical component into an interface of an object with an external environment, wherein a surface is provided adjacent the interface and separated by a gap from the interface, detecting, from incident radiation reflected from the interface and from the surface, radiation of a second different polarization state arising from the reflection of incident radiation of the first polarization at the interface as distinct from the radiation of the first polarization state in the reflected radiation, and producing a position signal representative of a relative position between the focus of the optical component and the object.

20 Claims, 14 Drawing Sheets

(51) Int. Cl.
*G03F 7/20* (2006.01)
*G02B 21/00* (2006.01)
*G01N 21/956* (2006.01)
*G01B 11/14* (2006.01)
*G02B 5/30* (2006.01)

(52) U.S. Cl.
CPC ..... *G02B 21/0016* (2013.01); *G03F 7/70308* (2013.01); *G03F 7/70591* (2013.01); *G03F 7/70625* (2013.01); *G03F 7/70633* (2013.01); *G02B 5/3025* (2013.01)

(58) Field of Classification Search
CPC .......... G03F 7/707941; G03F 7/70633; G03F 7/70641; G03F 7/70325; G03F 7/70341; G03F 7/7035; G03F 7/7085; G03F 7/70833; G03F 7/70566; G03F 7/70308; G03F 7/70375; G03F 7/70408; G11B 7/1387
USPC .. 355/30, 52, 53, 55, 58, 63, 67–71, 72, 77; 250/492.1, 492.2, 492.22, 492.23, 548; 356/364, 369, 124, 125, 614, 624
See application file for complete search history.

(56) References Cited

U.S. PATENT DOCUMENTS

| | | | |
|---|---|---|---|
| 8,411,287 B2 | 4/2013 | Smilde et al. | |
| 9,081,303 B2 | 7/2015 | Cramer et al. | |
| 2003/0174301 A1 | 9/2003 | Imanishi | |
| 2005/0030051 A1 | 2/2005 | Hanson et al. | |
| 2006/0066855 A1 | 3/2006 | Den Boef et al. | |
| 2007/0171778 A1* | 7/2007 | Saito | G11B 7/0901 369/44.23 |
| 2007/0217300 A1 | 9/2007 | Koyama et al. | |
| 2008/0212436 A1* | 9/2008 | Zijp | G11B 7/0908 369/53.19 |
| 2008/0279070 A1 | 11/2008 | Zijp et al. | |
| 2011/0027704 A1 | 2/2011 | Cramer et al. | |
| 2011/0043791 A1 | 2/2011 | Smilde et al. | |
| 2012/0044470 A1 | 2/2012 | Smilde et al. | |
| 2012/0294133 A1* | 11/2012 | Matsuzaki | G11B 7/0908 369/53.12 |
| 2013/0342831 A1* | 12/2013 | Levinski | G03F 7/70633 356/237.1 |

OTHER PUBLICATIONS

Yeh, Wei-Hung et al., "Evanescent coupling in magneto-optical and phase-change disk systems based on the solid immersion lens", Applied Optics, vol. 39, No. 2, pp. 302-315 (2000).

Chen, Tao et al., "Experimental investigation of photomask with near-field polarization Imaging", Proc. of SPIE, vol. 6349, pp. 634953-1-634953-8 (2006).

Mansfield, Scott Marshall, Ph.D., "Solid immersion microscopy", Published doctoral dissertation, Stanford University, University Microfilms International, 179 pages (1992).

* cited by examiner

METHOD AND APPARATUS FOR INSPECTION AND METROLOGY

CROSS-REFERENCE TO RELATED APPLICATIONS

This application is the U.S. national phase entry of PCT patent application no. PCT/EP2016/058640, which was filed on Apr. 19, 2016, which claims the benefit of priority of European patent application no. 15166233.5, which was filed on May 04, 2015, and which is incorporated herein in its entirety by reference.

FIELD

The present description relates to a method and apparatus to control a distance between two objects.

BACKGROUND

A lithographic apparatus is a machine that applies a desired pattern onto a substrate, usually onto a target portion of the substrate. A lithographic apparatus can be used, for example, in the manufacture of integrated circuits (ICs). In that instance, a patterning device, which is alternatively referred to as a mask or a reticle, may be used to generate a circuit pattern to be formed on an individual layer of the IC. This pattern can be transferred onto a target portion (e.g., including part of, one, or several dies) on a substrate (e.g., a silicon wafer). Transfer of the pattern is typically via imaging onto a layer of radiation-sensitive material (resist) provided on the substrate. In general, a single substrate will contain a network of adjacent target portions that are successively patterned. Known lithographic apparatus include so-called steppers, in which each target portion is irradiated by exposing an entire pattern onto the target portion at one time, and so-called scanners, in which each target portion is irradiated by scanning the pattern through a radiation beam in a given direction (the "scanning"-direction) while synchronously scanning the substrate parallel or anti parallel to this direction. It is also possible to transfer the pattern from the patterning device to the substrate by imprinting the pattern onto the substrate.

In order to monitor the lithographic process, the patterned substrate is inspected and one or more parameters of the patterned substrate are measured. The one or more parameters may include, for example, the overlay error between successive layers formed in or on the patterned substrate and/or critical linewidth of developed photosensitive resist. This measurement may be performed on a target of the product substrate itself and/or on a dedicated metrology target provided on the substrate. There are various techniques for making measurements of the microscopic structures formed in lithographic processes, including the use of a scanning electron microscope and/or various specialized tools.

A fast and non-invasive form of specialized inspection tool is a scatterometer in which a beam of radiation is directed onto a target on the surface of the substrate and properties of the scattered or reflected beam are measured. By comparing one or more properties of the beam before and after it has been reflected or scattered by the substrate, one or more properties of the substrate can be determined. Two main types of scatterometer are known. A spectroscopic scatterometer directs a broadband radiation beam onto the substrate and measures the spectrum (intensity as a function of wavelength) of the radiation scattered into a particular narrow angular range. An angle resolved scatterometer uses a relatively narrowband radiation beam and measures the intensity of the scattered radiation as a function of angle.

A particular application of scatterometry is in the measurement of feature asymmetry within a periodic target. This can be used as a measure of overlay error, for example, but other applications are also known. In an angle resolved scatterometer, asymmetry can be measured by comparing opposite parts of the diffraction spectrum (for example, comparing the $-1$st and $+1^{st}$ orders in the diffraction spectrum of a periodic grating). This can be done simply in angle-resolved scatterometry, as is described for example in U.S. patent application publication US2006-066855.

SUMMARY

With reduction of the physical dimensions in lithographic processing, there is demand to, for example, increase measurement precision and/or accuracy, and/or reduce the space occupied by targets dedicated to metrology or inspection. Image based scatterometry measurements have been devised to allow the use of smaller targets, by taking separate images of the target using $-1^{st}$ and $+1^{st}$ order radiation in turn. Examples of this image based technique are described in published U.S. patent application publication nos. US2011-0027704, US2011-0043791 and US2012-0044470, which are incorporated herein in their entirety by reference Demand for further reduction in target size and for improved accuracy and/or precision continues, however, and existing techniques suffer from various constraints that make it difficult to maintain accuracy and/or precision, and/or reduce the size of the targets. Another way to improve on inspection and measurement techniques is to use a solid immersion lens (SIL) as the optical element nearest the substrate surface. The extreme proximity of the SIL with the substrate surface (e.g., target surface) results in near-field radiation with a very high effective numerical aperture (NA) larger than 1. Using a coherent or incoherent radiation source with this SIL allows a very small target to be inspected.

To take advantage of the increasing numerical aperture, the gap between the SIL and the substrate needs to be set to a desired value. For example, the gap may be within the range of $\lambda/40$ to $\lambda/8$ (where $\lambda$ is the wavelength of the measurement radiation) e.g., within the range of 10-100 nm or 10-50 nm, to have the SIL in effective optical contact with the substrate. An example optical gap measuring method and apparatus can involve detecting cross components of polarization in the high numerical aperture element. The cross polarized signal is then recorded by a detector and can be used as an input parameter into a gap control process. This cross polarized signal may also be normalized by the cross polarized signal detected at a large gap of several wavelengths. In another example, the gap may be controlled by reference to reflected laser radiation intensity. With any detecting method, the gap between the SIL (or other component) and the substrate (or other surface) needs to be established to be, and maintained at, a desired gap distance or distance range.

With such small gap distances and various surface topographies possible (whether expected or unexpected due to process variations), it is desired to provide one or more methods and apparatus to control the position of a component relative to a surface at solid immersion gap distances. So, as a particular application, an embodiment may be applied to controlling a gap between an optical element and a reflective or diffractive surface for, e.g., inspection of a layer manufactured by a lithographic technique to measure overlay error or other one or more other parameters.

In an embodiment, there is provided a method, comprising: providing incident radiation of a first polarization state by an optical component into an interface of an object with an external environment, wherein a surface is provided adjacent the interface and separated by a gap from the interface; detecting, from incident radiation reflected from the interface and from the surface, radiation of a second different polarization state arising from the reflection of incident radiation of the first polarization at the interface as distinct from the radiation of the first polarization state in the reflected radiation; and producing a position signal representative of a relative position between the focus of the optical component and the object.

In an embodiment, there is provided a method, comprising: focusing radiation by an optical component into an object toward an interface of the object with an external environment; reflecting, at the interface, focused radiation by total internal reflection; detecting reflected radiation; and producing a position signal representative of the relative position between the focus of the optical component and the object based on the detected reflected radiation.

In an embodiment, there is provided a method, comprising: providing, by an optical component, radiation of a first polarization state into an object toward an interface of the object with an external environment; reflecting radiation from the interface, the reflected radiation comprising radiation of a second polarization state orthogonal to the first polarization state arising from the reflection of the radiation of the first polarization state at the interface; processing the reflected radiation to produced processed radiation having substantially only radiation of the second polarization state or having a higher proportion of the radiation of the second polarization state than the first polarization state relative to the reflected radiation; and detecting the processed radiation and producing a position signal representative of the position of the object and/or the component based on the detected processed radiation.

In an embodiment, there is provided a method, comprising: providing incident radiation by an optical component into an object toward an interface of the object with an external environment, wherein a surface is provided adjacent the interface and separated by a gap from the interface; processing reflected radiation arising from the reflection of the incident radiation at the interface and at the surface to reduce a proportion of radiation reflected from the surface in the reflected radiation; and producing a position signal representative of a position of the object and/or the component based on the processed radiation.

In an embodiment, there is provided a method, comprising: providing radiation that is circularly polarized by an optical component into an object toward an interface of the object with an external environment; and producing a position signal representative of a position of the object and/or objective based substantially only on radiation reflected from the interface arising from radiation incident at the interface at angles greater than a critical angle associated with the interface.

In an aspect, there is provided a method of manufacturing devices wherein a device pattern is applied to a series of substrates using a lithographic process, the method including inspecting at least a target formed as part of or beside the device pattern on at least one of the substrates using a method as described herein, and controlling the lithographic process for later substrates in accordance with the result of the method.

In an aspect, there is provided a non-transitory computer program product comprising machine-readable instructions for causing a processor to cause performance of a method as described herein.

In an aspect, there is provided a system comprising: an inspection apparatus configured to provide a beam on a measurement target on a substrate and to detect radiation redirected by the target to determine a parameter of a lithographic process; and a non-transitory computer program product as described herein.

BRIEF DESCRIPTION OF THE DRAWINGS

Embodiments will now be described, by way of example only, with reference to the accompanying drawings in which.

DETAILED DESCRIPTION

Before describing embodiments in detail, it is instructive to present an example environment in which embodiments may be implemented.

Figure 1:
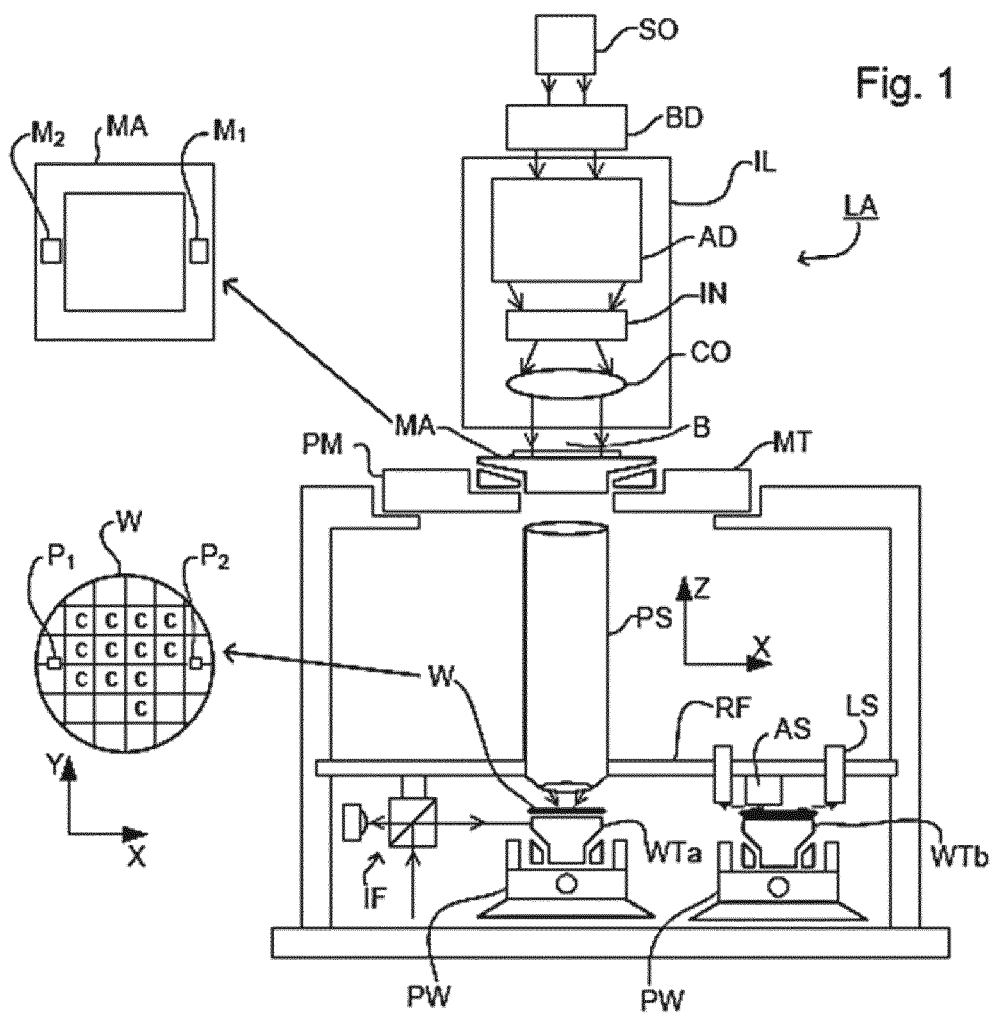
FIG. 1 schematically depicts an embodiment of a lithographic apparatus.

FIG. 1 schematically depicts a lithographic apparatus LA. The apparatus comprises:
- an illumination system (illuminator) IL configured to condition a radiation beam B (e.g. UV radiation or DUV radiation).
- a support structure (e.g. a mask table) MT constructed to support a patterning device (e.g. a mask) MA and connected to a first positioner PM configured to accurately position the patterning device in accordance with certain parameters;
- a substrate table (e.g. a wafer table) WT constructed to hold a substrate (e.g. a resist-coated wafer) W and connected to a second positioner PW configured to accurately position the substrate in accordance with certain parameters; and
- a projection system (e.g. a refractive projection lens system) PS configured to project a pattern imparted to the radiation beam B by patterning device MA onto a target portion C (e.g. comprising one or more dies) of the substrate W, the projection system supported on a reference frame (RF).

The illumination system may include various types of optical components, such as refractive, reflective, magnetic, electromagnetic, electrostatic or other types of optical components, or any combination thereof, for directing, shaping, or controlling radiation.

The support structure supports the patterning device in a manner that depends on the orientation of the patterning device, the design of the lithographic apparatus, and other conditions, such as for example whether or not the patterning device is held in a vacuum environment. The support structure can use mechanical, vacuum, electrostatic or other clamping techniques to hold the patterning device. The support structure may be a frame or a table, for example, which may be fixed or movable as required. The support structure may ensure that the patterning device is at a desired position, for example with respect to the projection system. Any use of the terms "reticle" or "mask" herein may be considered synonymous with the more general term "patterning device."

The term "patterning device" used herein should be broadly interpreted as referring to any device that can be used to impart a radiation beam with a pattern in its cross-section such as to create a pattern in a target portion of the substrate. It should be noted that the pattern imparted to the radiation beam may not exactly correspond to the desired pattern in the target portion of the substrate, for example if the pattern includes phase-shifting features or so called assist features. Generally, the pattern imparted to the radiation beam will correspond to a particular functional layer in a device being created in the target portion, such as an integrated circuit.

The patterning device may be transmissive or reflective. Examples of patterning devices include masks, programmable mirror arrays, deformable mirrors, and programmable LCD panels. Masks are well known in lithography, and include mask types such as binary, alternating phase-shift, and attenuated phase-shift, as well as various hybrid mask types. An example of a programmable mirror array employs a matrix arrangement of small mirrors, each of which can be individually tilted so as to reflect an incoming radiation beam in different directions. The tilted mirrors impart a pattern in a radiation beam, which is reflected by the mirror matrix.

The term "projection system" used herein should be broadly interpreted as encompassing any type of projection system, including refractive, reflective, catadioptric, magnetic, electromagnetic and electrostatic optical systems, or any combination thereof, as appropriate for the exposure radiation being used, or for other factors such as the use of an immersion liquid or the use of a vacuum. Any use of the term "projection lens" herein may be considered as synonymous with the more general term "projection system".

As here depicted, the apparatus is of a transmissive type (e.g. employing a transmissive mask). Alternatively, the apparatus may be of a reflective type (e.g. employing a programmable mirror array of a type as referred to above, or employing a reflective mask).

The lithographic apparatus may be of a type having two (dual stage) or more tables (e.g., two or more substrate tables WTa, WTb, two or more patterning device tables, a substrate table WTa and a table WTb below the projection system without a substrate that is dedicated to, for example, facilitating measurement, and/or cleaning, etc.). In such "multiple stage" machines the additional tables may be used in parallel, or preparatory steps may be carried out on one or more tables while one or more other tables are being used for exposure. For example, alignment measurements using an alignment sensor AS and/or level (height, tilt, etc.) measurements using a level sensor LS may be made.

The lithographic apparatus may also be of a type wherein at least a portion of the substrate may be covered by a liquid having a relatively high refractive index, e.g. water, so as to fill a space between the projection system and the substrate. An immersion liquid may also be applied to other spaces in the lithographic apparatus, for example, between the patterning device and the projection system. Immersion techniques are known in the art for increasing the numerical aperture of projection systems. The term "liquid immersion" as used herein does not mean that a structure, such as a substrate, must be submerged in liquid, but rather only means that liquid is located between the projection system and the substrate during exposure.

Further, the lithographic apparatus may also be of a type wherein at least an optical element is located in close proximity to a portion of the substrate resulting in near-field radiation spanning a gap between the optical element and the substrate. This may be referred to as solid immersion using a solid immersion lens/optical element.

Referring to FIG. 1, the illuminator IL receives a radiation beam from a radiation source SO. The source and the lithographic apparatus may be separate entities, for example when the source is an excimer laser. In such cases, the source is not considered to form part of the lithographic apparatus and the radiation beam is passed from the source SO to the illuminator IL with the aid of a beam delivery system BD comprising, for example, suitable directing mirrors and/or a beam expander. In other cases the source may be an integral part of the lithographic apparatus, for example when the source is a mercury lamp. The source SO and the illuminator IL, together with the beam delivery system BD if required, may be referred to as a radiation system.

The illuminator IL may comprise an adjuster AD configured to adjust the angular intensity distribution of the radiation beam. Generally, at least the outer and/or inner radial extent (commonly referred to as σ-outer and σ-inner, respectively) of the intensity distribution in a pupil plane of the illuminator can be adjusted. In addition, the illuminator IL may comprise various other components, such as an integrator IN and a condenser CO. The illuminator may be used to condition the radiation beam, to have a desired uniformity and intensity distribution in its cross-section.

The radiation beam B is incident on the patterning device (e.g., mask) MA, which is held on the support structure (e.g., mask table) MT, and is patterned by the patterning device. Having traversed the patterning device MA, the radiation beam B passes through the projection system PS, which focuses the beam onto a target portion C of the substrate W. With the aid of the second positioner PW and position sensor IF (e.g. an interferometric device, linear encoder, 2-D encoder or capacitive sensor), the substrate table WT can be moved accurately, e.g. so as to position different target portions C in the path of the radiation beam B. Similarly, the first positioner PM and another position sensor (which is not explicitly depicted in FIG. 1) can be used to accurately position the patterning device MA with respect to the path of the radiation beam B, e.g. after mechanical retrieval from a mask library, or during a scan. In general, movement of the support structure MT may be realized with the aid of a long-stroke module (coarse positioning) and a short-stroke module (fine positioning), which form part of the first positioner PM. Similarly, movement of the substrate table WT may be realized using a long-stroke module and a short-stroke module, which form part of the second positioner PW. In the case of a stepper (as opposed to a scanner) the support structure MT may be connected to a short-stroke actuator only, or may be fixed. Patterning device MA and substrate W may be aligned using patterning device alignment marks M1, M2 and substrate alignment marks P1, P2. Although the substrate alignment marks as illustrated occupy dedicated target portions, they may be located in spaces between target portions (these are known as scribe-lane alignment marks). Similarly, in situations in which more than one die is provided on the patterning device MA, the patterning device alignment marks may be located between the dies.

The depicted apparatus could be used in at least one of the following modes:

1. In step mode, the support structure MT and the substrate table WT are kept essentially stationary, while an entire pattern imparted to the radiation beam is projected onto a target portion C at one time (i.e. a single static exposure). The substrate table WT is then shifted in the X and/or Y direction so that a different target portion C can be exposed. In step mode, the maximum size of the exposure field limits the size of the target portion C imaged in a single static exposure.

2. In scan mode, the support structure MT and the substrate table WT are scanned synchronously while a pattern imparted to the radiation beam is projected onto a target portion C (i.e. a single dynamic exposure). The velocity and direction of the substrate table WT relative to the support structure MT may be determined by the (de-)magnification and image reversal characteristics of the projection system PS. In scan mode, the maximum size of the exposure field limits the width (in the non-scanning direction) of the target portion in a single dynamic exposure, whereas the length of the scanning motion determines the height (in the scanning direction) of the target portion.

3. In another mode, the support structure MT is kept essentially stationary holding a programmable patterning device, and the substrate table WT is moved or scanned while a pattern imparted to the radiation beam is projected onto a target portion C. In this mode, generally a pulsed radiation source is employed and the programmable patterning device is updated as required after each movement of the substrate table WT or in between successive radiation pulses during a scan. This mode of operation can be readily applied to maskless lithography that utilizes programmable patterning device, such as a programmable mirror array of a type as referred to above.

Combinations and/or variations on the above described modes of use or entirely different modes of use may also be employed.

Figure 2:
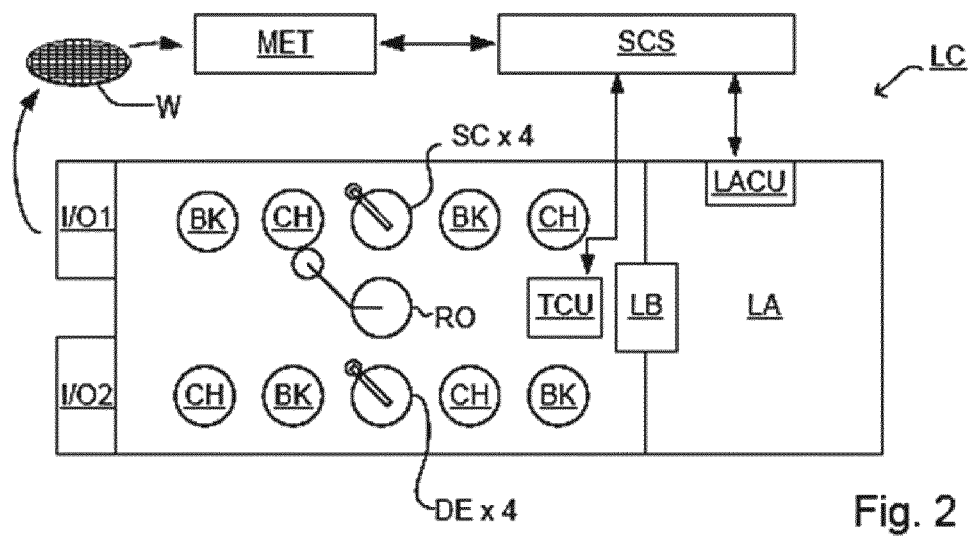
FIG. 2 schematically depicts an embodiment of a lithographic cell or cluster.

As shown in FIG. 2, the lithographic apparatus LA forms part of a lithographic cell LC, also sometimes referred to a lithocell or cluster, which also includes apparatuses to perform pre- and post-exposure processes on a substrate. Conventionally these include one or more spin coaters SC to deposit one or more resist layers, one or more developers DE to develop exposed resist, one or more chill plates CH and/or one or more bake plates BK. A substrate handler, or robot, RO picks up one or more substrates from input/output port I/O1,I/O2, moves them between the different process apparatuses and delivers them to the loading bay LB of the lithographic apparatus. These apparatuses, which are often collectively referred to as the track, are under the control of a track control unit TCU which is itself controlled by the supervisory control system SCS, which also controls the lithographic apparatus via lithography control unit LACU. Thus, the different apparatuses can be operated to maximize throughput and processing efficiency.

In order that a substrate that is exposed by the lithographic apparatus is exposed correctly and consistently, it is desirable to inspect an exposed substrate to measure one or more properties such as overlay error between subsequent layers, line thickness, critical dimension (CD), etc. Accordingly a manufacturing facility in which lithocell LC is located also typically includes a metrology/inspection system MET which receives some or all of the substrates W that have been processed in the lithocell. The metrology/inspection system MET may be part of the lithocell LC, for example it may be part of the lithographic apparatus LA.

Metrology/inspection results may be provided directly or indirectly to the supervisory control system SCS. If an error is detected, an adjustment may be made to exposure of a subsequent substrate (especially if the inspection can be done soon and fast enough that one or more other substrates of the batch are still to be exposed) and/or to subsequent exposure of the exposed substrate. Also, an already exposed substrate may be stripped and reworked to improve yield, or discarded, thereby avoiding performing further processing on a substrate known to be faulty. In a case where only some target portions of a substrate are faulty, further exposures may be performed only on those target portions which are good.

Within a metrology/inspection system MET, an inspection apparatus is used to determine one or more properties of the substrate, and in particular, how one or more properties of different substrates vary or different layers of the same substrate vary from layer to layer. The inspection apparatus may be integrated into the lithographic apparatus LA or the lithocell LC or may be a stand-alone device. To enable rapid measurement, it is desirable that the inspection apparatus measure one or more properties in the exposed resist layer immediately after the exposure. However, the latent image in the resist has a low contrast—there is only a very small difference in refractive index between the parts of the resist which have been exposed to radiation and those which have not—and not all inspection apparatus have sufficient sensitivity to make useful measurements of the latent image. Therefore measurements may be taken after the post-exposure bake step (PEB) which is customarily the first step carried out on an exposed substrate and increases the contrast between exposed and unexposed parts of the resist. At this stage, the image in the resist may be referred to as semi-latent. It is also possible to make measurements of the developed resist image—at which point either the exposed or unexposed parts of the resist have been removed—or after a pattern transfer step such as etching. The latter possibility limits the possibilities for rework of a faulty substrate but may still provide useful information.

Figure 3:
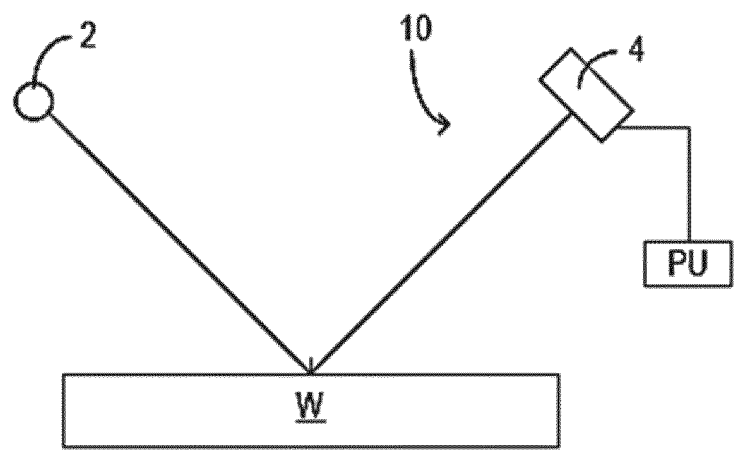
FIG. 3 schematically depicts an example inspection apparatus and metrology technique.
Figure 3:
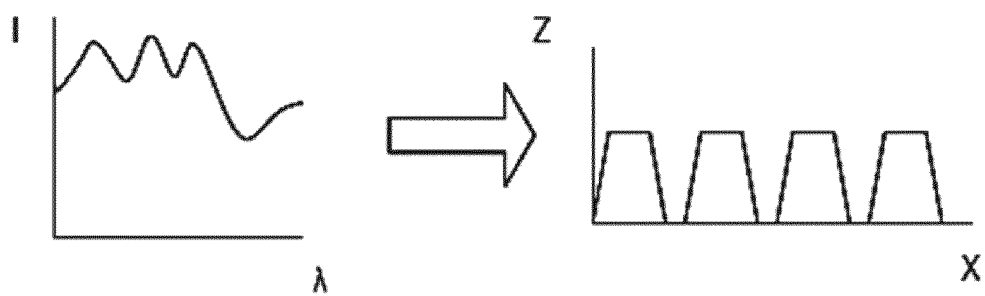

FIG. 3 depicts an example inspection apparatus (e.g., a scatterometer). It comprises a broadband (white light) radiation projector 2 which projects radiation onto a substrate W. The reflected radiation is passed to a spectrometer detector 4, which measures a spectrum 10 (intensity as a function of wavelength) of the specular reflected radiation, as shown, e.g., in the graph in the lower left. From this data, the structure or profile giving rise to the detected spectrum may be reconstructed by processor system PU, e.g. by Rigorous Coupled Wave Analysis and non-linear regression or by comparison with a library of simulated spectra as shown at the bottom right of FIG. 3. In general, for the reconstruction the general form of the structure is known and some parameters are assumed from knowledge of the process by which the structure was made, leaving only a few parameters of the structure to be determined from the measured data. Such an inspection apparatus may be configured as a normal-incidence inspection apparatus or an oblique-incidence inspection apparatus.

Figures 4, 5:
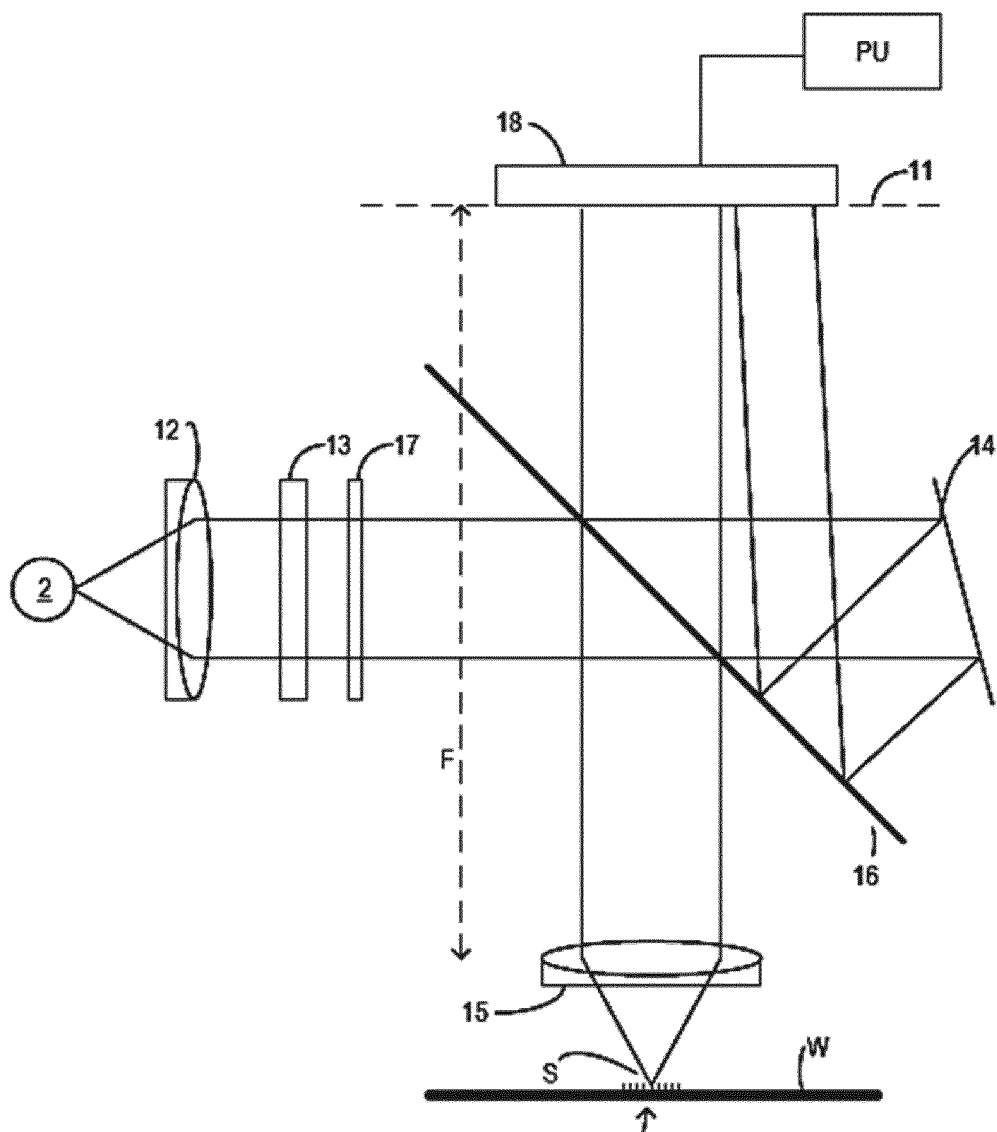
FIG. 4 schematically depicts an example inspection apparatus.
FIG. 5 illustrates the relationship between an illumination spot of an inspection apparatus and a metrology/inspection target.

Another inspection apparatus that may be used is shown in FIG. 4. In this device, the radiation emitted by radiation source 2, which may be coherent or incoherent, is collimated using lens system 12 and transmitted through interference filter 13 and polarizer 17, reflected by partially reflecting surface 16 and is focused into a spot S on substrate W via an objective lens 15, which has a high numerical aperture (NA), desirably at least 0.9 or at least 0.95. A solid immersion inspection apparatus (using near-field radiation between an objective of the apparatus and the target) and/or a liquid immersion inspection apparatus (using a relatively high refractive index fluid such as water) may even have a numerical aperture over 1.

As in the lithographic apparatus LA, one or more substrate tables may be provided to hold the substrate W during measurement operations. The substrate tables may be similar or identical in form to the substrate tables WTa, WTb of FIG. 1. In an example where the inspection apparatus is integrated with the lithographic apparatus, they may even be the same substrate table. Coarse and fine positioners may be provided to a second positioner PW configured to accurately position the substrate in relation to a measurement optical system. Various sensors and actuators are provided for example to acquire the position of a target of interest, and to bring it into position under the objective lens 15. Typically many measurements will be made on targets at different locations across the substrate W. The substrate support can be moved in X and Y directions and optionally rotated around the Z direction to acquire different targets, and in the Z direction to obtain a desired location of the target relative to the focus of the optical system. It is convenient to think and describe operations as if the objective lens is being brought to different locations relative to the substrate, when, for example, in practice the optical system may remain substantially stationary (typically in the X and Y directions, but perhaps also in the Z direction) and only the substrate moves. Provided the relative position of the substrate and the optical system is correct, it does not matter in principle which one of those is moving in the real world, or if both are moving, or a combination of a part of the optical system is moving (e.g., in the Z and/or tilt direction) with the remainder of the optical system being stationary and the substrate is moving (e.g., in the X and Y directions, but also optionally in the Z and/or tilt direction).

The radiation redirected by the substrate W then passes through partially reflecting surface 16 into a detector 18 in order to have the spectrum detected. The detector may be located in a back-projected pupil plane or back focal plane (or a conjugate plane thereof) 11 of the lens system 15, which is at the focal length of the lens system 15, however the back-projected pupil plane or back focal plane may instead be re-imaged with auxiliary optics (not shown) onto the detector. The pupil plane is the plane in which the radial position of radiation defines the angle of incidence and the angular position defines azimuth angle of the radiation. The detector may be a two-dimensional detector so that a two-dimensional angular scatter spectrum of a substrate target 30 can be measured. The detector 18 may be, for example, an array of CCD or CMOS sensors, and may use an integration time of, for example, 40 milliseconds per frame.

A reference beam may be used, for example, to measure the intensity of the incident radiation. To do this, when the radiation beam is incident on the partially reflecting surface 16 part of it is transmitted through the partially reflecting surface 16 as a reference beam towards a reference mirror 14. The reference beam is then projected onto a different part of the same detector 18 or alternatively on to a different detector (not shown).

One or more interference filters 13 are available to select a wavelength of interest in the range of, say, 405-790 nm or even lower, such as 100-350 nm. The interference filter may be tunable rather than comprising a set of different filters. A grating could be used instead of an interference filter. An aperture stop or spatial light modulator (not shown) may be provided in the illumination path to control the range of angle of incidence of radiation on the target.

The detector 18 may measure the intensity of redirected radiation at a single wavelength (or narrow wavelength range), the intensity separately at multiple wavelengths or integrated over a wavelength range. Furthermore, the detector may separately measure the intensity of transverse magnetic-and transverse electric-polarized radiation and/or the phase difference between the transverse magnetic-and transverse electric-polarized radiation.

The target 30 on substrate W may be a 1-D grating, which is printed such that after development, the bars are formed of solid resist lines. The target 30 may be a 2-D grating, which is printed such that after development, the grating is formed of solid resist pillars or vias in the resist. The bars, pillars or vias may be etched into the substrate. The pattern (e.g., of bars, pillars or vias) is sensitive to aberrations in the lithographic projection apparatus, particularly the projection system PS, and illumination symmetry and the presence of such aberration will manifest in a variation in the printed grating. Accordingly, the measured data of the printed grating is used to reconstruct the grating. One or more parameters of the 1-D grating, such as line width and/or shape, or one or more parameters of the 2-D grating, such as pillar or via width or length or shape, may be input to the reconstruction process, performed by processor system PU, from knowledge of the printing step and/or other inspection processes.

In addition to measurement of a parameter by reconstruction, angle resolved scatterometry is useful in the measurement of asymmetry of features in product and/or resist patterns. A particular application of asymmetry measurement is for the measurement of overlay, where the target 30 comprises one set of periodic features superimposed on another. The concepts of asymmetry measurement using the instrument of FIG. 3 or FIG. 4 are described, for example, in U.S. patent application publication US2006-066855, which is incorporated herein in its entirety. Simply stated, while the positions of the diffraction orders in the diffraction spectrum of the target are determined only by the periodicity of the target, asymmetry in the diffraction spectrum is indicative of asymmetry in the individual features which make up the target. In the instrument of FIG. 4, where detector 18 may be an image sensor, such asymmetry in the diffraction orders appears directly as asymmetry in the pupil image recorded by detector 18. This asymmetry can be measured by digital image processing in processor system PU, and calibrated against known values of overlay.

FIG. 5 illustrates a plan view of a typical target 30, and the extent of illumination spot S in the apparatus of FIG. 4. To obtain a diffraction spectrum that is free of interference from surrounding structures, the target 30, in an embodiment, is a periodic structure (e.g., grating) larger than the width (e.g., diameter) of the illumination spot S. The width of spot S may be greater than or equal to 5, 10 or 20 µm and the target width a and/or target length may be 10, 12, 15, 20, 30 or 40 µm. The target in other words is 'underfilled' by the illumination, and the diffraction signal is free from interference by product features and the like outside the target itself. The illumination arrangement 2, 12, 13, 17 may be configured to provide illumination of a uniform intensity across a pupil plane of objective 15. Alternatively, by, e.g., including an aperture in the illumination path, illumination may be restricted to on axis or off axis directions or may be modified with an apodization filter.

But, there is demand to reduce the space occupied by metrology targets.

For example, there is a desire to, for example, reduce the width of 'scribe lanes' between target portions C on the substrate, where metrology targets have conventionally been located. Additionally or alternatively, there is a desire, for example, to include metrology targets within the device patterns themselves, to allow more precise and/or accurate monitoring and correction of variations in parameters such as CD and/or overlay. To this end, alternative methods of diffraction based metrology have been devised more recently. For example, in image-based metrology, two images of the target are made, each using different selected orders of the diffraction spectrum. Comparing the two images, one can obtain asymmetry information. By selecting parts of the images, one can separate the target signal from its surroundings. The targets can be made smaller, and need not be square, so that several can be included within the same illumination spot. Examples of this technique are described in U.S. patent application publications US2011-0027704, US2011-0043791, and US2012-0044470.

In addition to or alternatively to reducing the space occupied by metrology targets, there is demand to improve the nature of the measurements themselves, such as their accuracy and/or precision. For example, there is a desire to obtain higher sensitivity of measurement. Additionally or alternatively, there is a desire to, for example, obtain better decoupling between various parameters in the reconstruction described above. For example, it is desired to obtain better values for each of the specific parameters of interest, by reducing or eliminating the effect of measurements associated with one parameter of interest influencing another parameter of interest.

As the demand for size reduction and/or accuracy continues, existing techniques may meet some technical limitations. For example, some methods desire to capture at least the $\pm 1^{st}$ diffraction orders. Taking into account the numerical aperture of the objective 15, this constrains the pitch (L) of a periodic structure of the target. To improve sensitivity and/or to reduce target size, one can consider using shorter wavelengths $\lambda$. Further, the target cannot be too small otherwise it will not have enough features to be considered as a periodic structure (e.g., at least 15 lines may be required which taking into account previous constraints may fix the minimum periodic structure size around 2 µm×2 µm). Consequently, overlay, as an example, is measured using periodic structures features (e.g., lines) having dimensions far bigger than those of the product (e.g., device) layout, making overlay measurement less reliable. Ideally the feature line and pitch should have similar dimensions to the product features.

Figure 6:
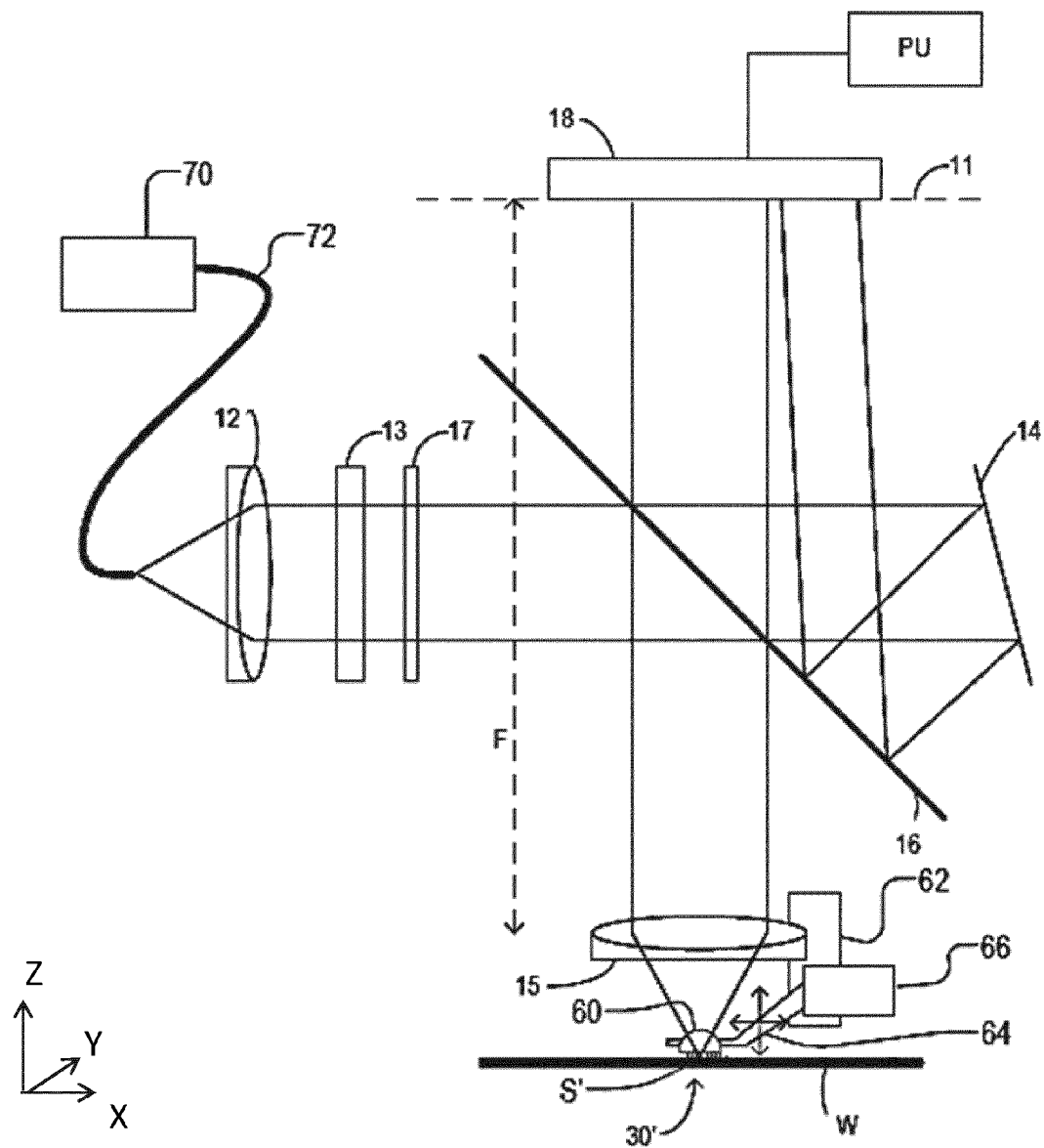
FIG. 6 depicts an example inspection apparatus comprising a solid immersion lens (SIL)

FIG. 6 shows an inspection apparatus in which improvement of the nature of the measurements themselves (e.g., precision and/or accuracy) and/or reduction of target size may be realized. In FIG. 6, a spot S' (which may be smaller than convention if, for example, a smaller target is desired) can be applied to a target 30' (which may be smaller than convention, e.g., features of smaller pitch, if, for example, a smaller target is desired). Like reference numerals refer to like components throughout the figures.

Comparing the apparatus of FIG. 6 with that of FIG. 4, a first difference is the provision of an additional optical element 60 close to the target 30'. This additional optical element is a miniature solid immersion lens (SIL), with a width (e.g., diameter) only on the order of a millimeter, for example in the range of 1 mm to 5 mm, for example about 2 mm. The SIL comprises, in an example, a hemisphere of material that receives rays of radiation at substantially normal incidence to its surface. In an embodiment, the SIL may be a different shape such as a super-hemisphere. In an embodiment, the SIL is made up of a material of refractive index n, such as glass, fused quartz, crystal, a combination of materials, etc. In an embodiment, the refractive index n is relatively high, e.g., greater than or equal to about 1.5, greater than or equal to about 1.8, greater than or equal to about 2 or greater than or equal to about 2.2. Within the SIL material, the numerical aperture (NA) of the original rays is multiplied by n. The received rays come to focus at about the center of the hemisphere or at the aplanatic point of a super-hemisphere and form a spot that is smaller by a factor of n compared to what would have been in the absence of the SIL. For example, a typical glass hemisphere having n=2 will reduce the width of the focused spot by a factor of 2.

When an objective of numerical aperture $NA_o$ focuses inside a hemispherical SIL, the numerical aperture of the combined system becomes $NA=n_{SIL} NA_o$ inside the SIL, where $n_{SIL}$ is the refractive index of the SIL. With, for example, a high NA objective of $NA_o=0.9$ and a SIL with $n_{SIL}=2$, a hyper-NA value of NA=1.8 may be achieved; while, an alternative more-than-hemispherical SIL design in combination with a high NA objective can result in a hyper-NA value of $NA=n_{SIL}^2 NA_o$. Such a hyper-NA optical configuration can improve the metrology capability of an inspection apparatus when the distance between the SIL and the target is significantly less than the wavelength of the radiation used or when a refractive index matching liquid is used.

When the distance between the SIL and the surface W (such as one or more structured or unstructured layers deposited on substrate W) exceeds approximately half a wavelength of the radiation beam (whether a beam for inspection of the target, a beam for position measuring, etc.), then rays that are focused inside the SIL 60 at angles a to the optical axis with $n_{SIL} \sin\alpha > 1$ are fully reflected at the planar interface of the SIL tip and an environment (e.g., gas such as air) between the tip and the surface W with a refractive index of about 1, by total internal reflection (TIR). Thus, TIR limits the effective numerical aperture of the illumination of the surface W to about 1. However, when the distance between the SIL and the surface is significantly less than half the wavelength λ, (e.g., less than approximately λ/10), strong evanescent coupling between the $n_{SIL} \sin\alpha > 1$ rays and the surface W occurs. This evanescent coupling increases the effective numerical aperture to, e.g., about 1.8 as described above. This phenomenon is known as frustrated total internal reflection (FTIR) or evanescent coupling. In such a case, the SIL and the surface W may be considered as being in optical contact without being in actual mechanical contact. Therefore, under FTIR conditions, illumination of a surface W and detection of the radiation scattered by the surface W is possible with values for the numerical aperture exceeding 1 (hyper-NA).

Immersion of optical elements in liquid has been used to increase resolution in microscopy and photolithography. The solid immersion lens may achieve similar gains without the inconvenience/problems of liquid immersion. However, the bottom of the SIL must either be in contact with the target 30 or positioned extremely closely to it. This restricts its practical applications.

A so-called micro-SIL may also be used. The width (e.g., diameter) of such a SIL is many times smaller, for example about 2 microns in width instead of about 2 millimeters. In an example where SIL 60 in the FIG. 6 apparatus is a micro-SIL, it may have a width (e.g., diameter) less than or equal to 10 μm, potentially less than or equal to 5 μm.

Whether a miniature SIL 60 or a micro-SIL is used, it can be attached to a movable support so that controlling the alignment and proximity to the substrate is much simpler than in the case of a lens with bigger width. For example, the SIL 60 in FIG. 6 is mounted to a frame 62. In an embodiment, frame 62 is movable. An actuator may be provided to move frame 62. In an embodiment, the frame 62 supports the objective 15. Accordingly, in an embodiment, the frame 62 may move both the objective 15 and the SIL 60 together. In an embodiment, the actuator for the frame 62 may be configured to move the frame 62 (and the SIL 60) in substantially the Z direction. In an embodiment, the actuator for the frame 62 may be configured to move the frame 62 (and the SIL 60) around the X axis and/or Y axis. In an embodiment, the SIL 60 is in relative fixed position relative to the frame 62. In an embodiment, the objective 15 is movable relative to the frame 62 by, e.g., an actuator.

As noted above, the SIL 60 in FIG. 6 is mounted to a frame 62, which in an embodiment supports objective 15. Of course, the SIL 60 may be mounted on a separate frame from that supporting objective 15. In an embodiment, the SIL 60 is connected to a frame (e.g., frame 62) via a structure 64 and actuator 66. Actuator 66 may be, for example, piezoelectric in operation or voice coil actuated. The arrangement where the SIL 60 has an actuator to cause relative movement between a movable objective 15 and the SIL 60 may be referred to as a dual stage arrangement. In a dual stage, certain functionalities may be separated, e.g. separation of motion ranges, vibration suppression capabilities, SIL positioning and focusing with respect to the surface. In an embodiment, the objective stage may move only substantially in the Z-direction (substantially/essentially normal to the surface). In an embodiment, the SIL stage may move in more than 1 degree of freedom, e.g., at least 3 degrees of freedom, e.g., in the Z-direction and around the X-axis and/or the Y-axis, to position the SIL substantially/essentially parallel to the surface. The SIL stage may not have a mechanical range sufficient to cover the desired full travel range. So, the SIL stage can be used to position the SIL at a certain small distance above the surface, while the objective stage can position the objective at focus with respect to the surface, or with respect to the SIL.

Actuator 66 may operate in combination with one or more other actuators positioning the objective as a whole in relation to the target. The control loops of these different positioners can be integrated with one another. The components 62, 64 and 66, together with the substrate table and positioners (mentioned above but not shown in FIG. 6), form a support apparatus for positioning the SIL and the target 30 in close proximity to one another. As noted above, in principle, SIL 60 could be mounted rigidly to the frame 62, and/or may be of larger width. The separate structure and actuator allows easier control of the very small gap, as discussed in more detail below.

The SIL 60 works by capturing the near-field radiation from the target, and to this end it is positioned substantially closer than one wavelength ($\lambda$) of radiation from the target structure, generally closer than a half wavelength. The closer the distance, the stronger will be the coupling of near-field signals into the instrument. The gap between the SIL 60 and target 30' may therefore be less than $\lambda/4$, for example in the range of $\lambda/40$-$\lambda/8$ or in the range of $\lambda/10$-$\lambda/20$. Because the NA of the inspection apparatus is effectively increased, the pitch of the target periodic structure may be reduced closer to product dimensions.

In examples where a micro-SIL would be used, incoherent radiation of the type conventionally used in, for example, a scatterometer cannot be focused to a micron-sized spot as small as the micro-SIL. Accordingly, in such an embodiment the radiation source 2 may be changed to a coherent source. Therefore a laser source 70 is coupled to illumination optics 12, etc. via an optical fiber 72. The limit on the spot size on the substrate is set by the numerical aperture of the focusing lens system and the laser wavelength. As an additional benefit of using spatially coherent radiation, the instrument with laser radiation source 70 can be used to perform different types of scatterometry or measurement. For example, coherent Fourier scatterometry (CFS) may be used to measure the target.

As highlighted above, a small gap should be maintained between the SIL and the target. As also highlighted above, known techniques for controlling the gap have limitations, particularly when a variety of different target structures and materials are to be inspected.

For example, a significant challenge is to control a relatively small solid immersion lens (SIL) with a gap selected from the range of between $\lambda/40$ and $\lambda/4$, e.g., 10-100 nm between the SIL and the measured surface with a small (e.g., about 1-10% of the gap size) control error, subject to possibly much larger vibrations caused by external disturbances, e.g., vibrations of up to 300 nm. This may be achieved with a high-bandwidth control using a signal representative of the gap distance, e.g., a gap error signal (GES).

Figure 7:
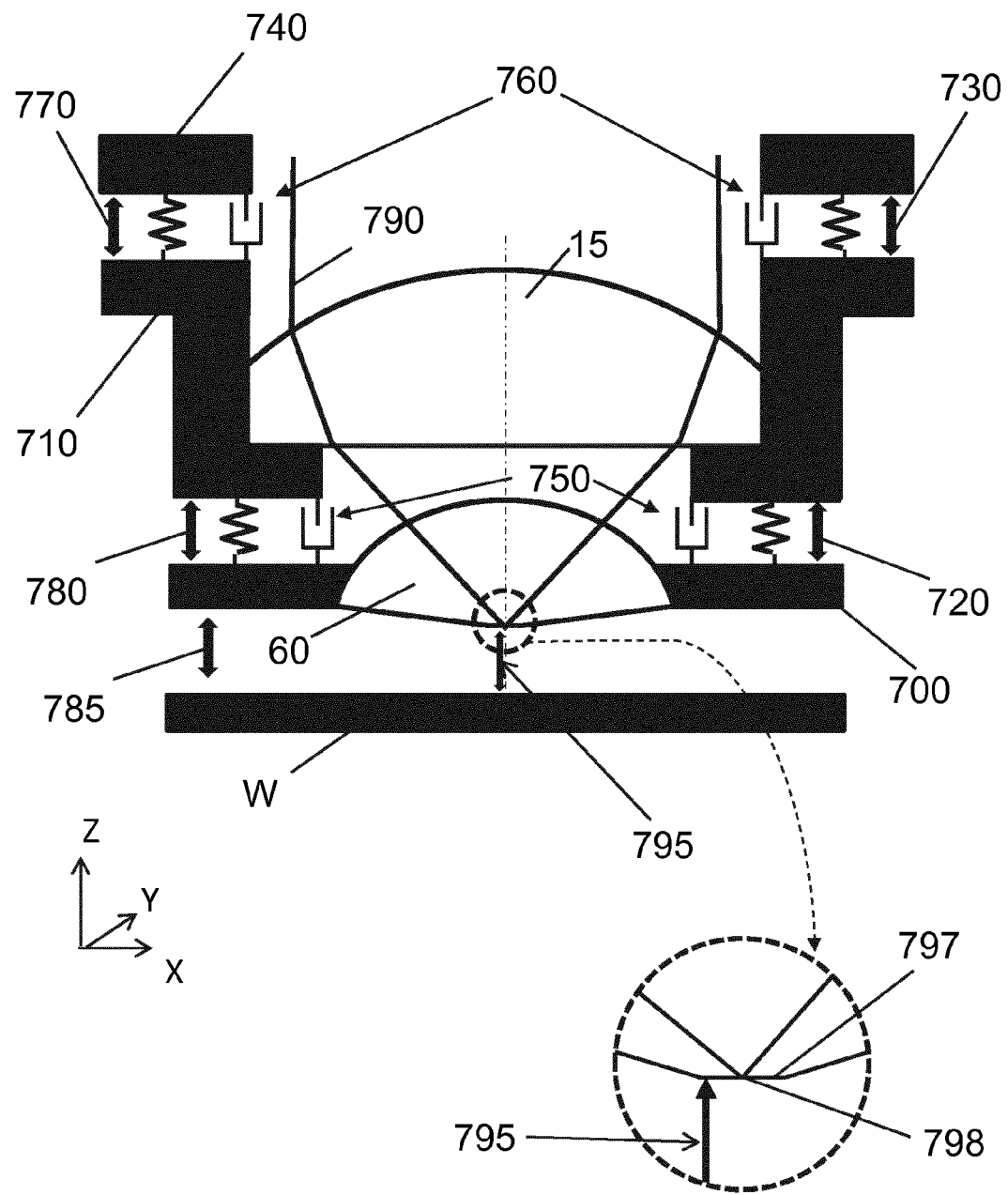
FIG. 7 depicts a schematic diagram of specific components of an inspection apparatus in relation to a target surface.

A "dual stage" concept may be used to facilitate positioning of the SIL and the objective close to the measured surface and allows for certain functionalities to be separated, e.g. separation of motion ranges, vibration suppression capabilities, SIL positioning and/or focusing with respect to the surface. Referring to FIG. 7, an embodiment of a "dual stage" concept is schematically depicted. A SIL 60 is attached to a movable support 700 to facilitate controlling the alignment and proximity of the SIL 60 to the measured surface, in this case the substrate W. This may be termed the SIL stage. Further, an objective 15 is attached to a movable support 710 to facilitate controlling the alignment and proximity of the SIL 60 and the objective 15 to the measured surface, in this case the substrate W. This may be termed the objective stage.

An actuator 720 may be provided to move the movable support 700 and the SIL 60 with respect to the movable support 710 and/or objective 15. An actuator 730 may be provided to move the movable support 710 and objective 15 with respect to a support 740. In this embodiment, the movable support 700 is mounted on the movable support 710 and so movement of the movable support 710 may also cause the movable support 700 and/or the SIL 60 to move. Accordingly, in an embodiment, the movable support 710 may move both the objective 15 and the SIL 60 together. Actuator 720 and/or 730 may be, for example, piezoelectric in operation or voice coil actuated.

The SIL stage may be mechanically suspended relative to the objective stage, which is represented by an equivalent spring and/or damping 750. The spring and/or damping 750 may be incorporated in the actuator 720 and/or provided separately by appropriate spring and/or damper structure. Similarly, the objective stage may be mechanically suspended relative to the support 740, which is represented by an equivalent spring and/or damping 760. The spring and/or damping 760 may be incorporated in the actuator 730 and/or provided separately by appropriate spring and/or damper structure.

In an embodiment, the actuator 720 may be configured to move the movable support 700 (and the SIL 60) in substantially the Z direction. In an embodiment, the actuator 720 may be configured to move the movable support 700 (and the SIL 60) around the X axis and/or Y axis. In an embodiment, the actuator 730 may be configured to move the movable support 710 (and the objective 15) in substantially the Z direction. In an embodiment, the actuator 730 may be configured to move the movable support 710 (and the objective 15) around the X axis and/or Y axis. In an embodiment, the objective stage may move only substantially in the Z-direction (substantially normal to the surface). In an embodiment, the SIL stage may move in more than 1 degree of freedom, e.g., at least 3 degrees of freedom, e.g., in the Z-direction and around the X-axis and/or the Y-axis, to position the SIL substantially parallel to the surface. The SIL stage may not have a mechanical range sufficient to cover the desired full travel range. So, the SIL stage can be used to position the SIL at a certain small distance above the surface, while the objective stage can position the objective at focus with respect to the surface, or with respect to the SIL.

Further, in an embodiment, the surface W itself may be moved. For example, a substrate table WT having the surface W may move the surface W relative to the SIL 60 to facilitate establishing an appropriate gap between the SIL 60 and the surface W.

To enable such positioning, one or more signals may be provided. For example, one or more signals 770 may be provided to enable positioning of the objective 15 and/or SIL 60 relative to the support 740 and/or to the surface W. Similarly, one or more signals 780 may be provided to enable positioning of the SIL 60 relative to the objective 15 and/or to the surface W. One or more signals 785 may be provided to enable positioning of the SIL 60 relative to the surface W. As an example, a signal 770 to enable relative positioning between the objective 15 and the support 740 may be provided by an encoder, a gas sensor, or an interferometer.

As described in more detail below, a signal 770 to enable relative positioning between the objective 15/SIL 60 and the surface W may be a signal derived from a radiation beam 790 passing through the objective 15, the SIL 60 and onto the surface W. As shown in the inset of FIG. 7, the radiation beam 790 may have a focus 798 located at the tip 797 of the SIL 60. In an embodiment, the tip 797 of the SIL 60 comprises a planar surface. The radiation beam 790 may be a dedicated beam for determining the position or may be the beam used to measure the surface but used for a certain time as a position measuring beam. A signal 780 to enable relative positioning between the objective 15 and the SIL 60 may be a focus error signal (FES). A signal 785 to enable relative positioning between the SIL 60 and the surface W may be a gap error signal (GES) as described herein.

So, the actuators 720 and 730 may operate in combination to position the objective 15 and the SIL 60 in relation to the surface W to establish a desired gap 795. A control system is provided to control positioning of the SIL 60 close to the surface W and to maintain the SIL 60 at or around that position. The control system may receive a setpoint gap value and control one or more actuators (e.g., actuators 720 and/730) to position, in one or more motions, the SIL 60 at or near the setpoint gap value and maintain the SIL 60 at or around that position. There may be significant relative vibrations between the surface W and the SIL 60. So, the SIL 60 may be controlled via a high-bandwidth (e.g., 1-10 kHz) feedback control system. To enable the control by the control system, the gap between the SIL 60 and the surface W may be represented by one or more signals, e.g., a gap error signal (GES). Various techniques for measuring the GES or other position signals are known in the art.

In an embodiment, the actuator 720 may be considered a fine positioner and the actuator 730 may be considered a coarse positioner. In an embodiment for motion in the Z-direction (e.g., vertical motion), a "dual stage" system may enable control of both the (1) focus between the objective 15 and the SIL 60, and (2) the gap 795 between the SIL 60 and the surface W.

Figure 8:
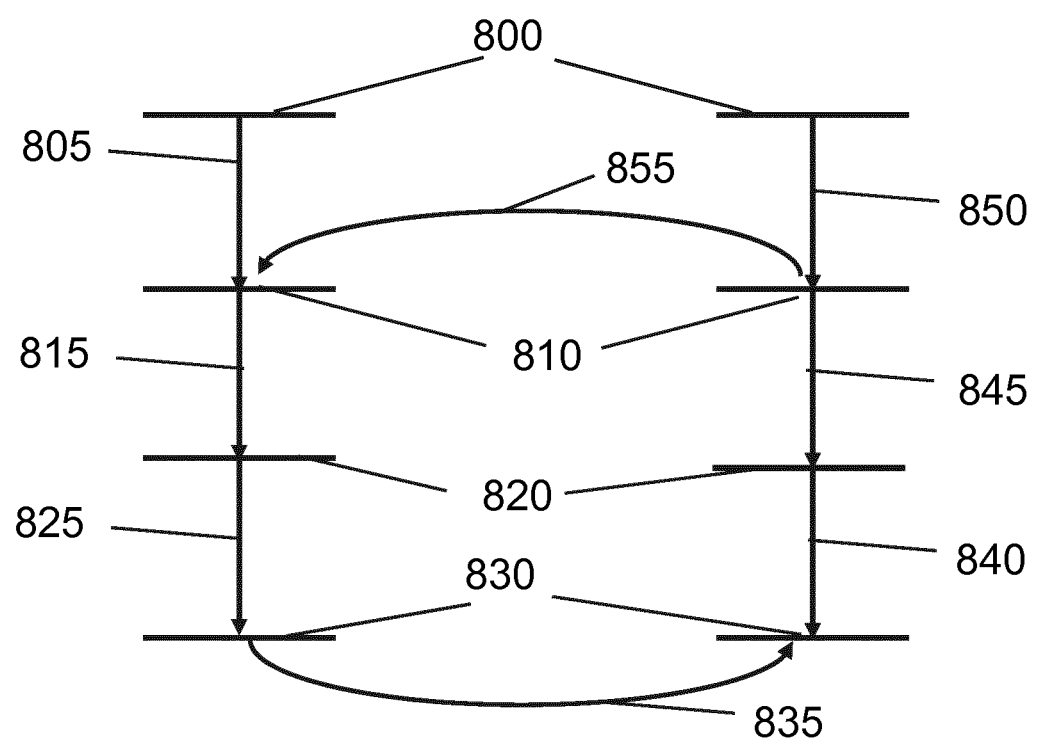
FIG. 8 depicts a schematic representation of various setpoints for relative positioning of various specific components of an inspection apparatus in relation to a target surface.

Further, a "dual stage" system can enable a relatively large dynamic range for the gap 795, e.g., about mm range with sub-10 nm accuracy. Referring to FIG. 8, an embodiment of Z-direction motion set points is schematically described. A first setpoint distance 800 may be defined for the distance of the SIL 60 from the surface W (i.e., gap 795) to enable exchange of a surface to be measured (e.g., substrate W) with another surface to be measured. In an embodiment, the first setpoint distance 800 may be selected from the range of about several millimeters, e.g., about 1-5 mm, or about 1 mm. Once a surface W to be measured is in place, the SIL 60 may be positioned closer to the surface W in an approach motion 805 to a second setpoint distance 810 of the gap 795. In an embodiment, the second setpoint distance 810 may be selected from the range of about several hundreds of microns down to several tens of microns, e.g., 400 to 50 microns, e.g., about 150 to 350 microns, e.g., about 300 microns. The second setpoint distance 810 enables relatively safe relative movement between the surface W and the SIL 60, for example, to horizontally position the SIL 60 over a target 30.

From the second setpoint distance 810, the SIL 60 may be positioned closer to the surface W in an approach motion 815 to a third setpoint distance 820 of the gap 795. In an embodiment, the third setpoint distance 820 may be selected from the range of half a wavelength, e.g., about 350 to 100 nanometers, e.g., about 350 to 175 nanometers, e.g., about 300 nanometers. The third setpoint distance 820 may be the maximum gap 795 for which the GES can be used.

From the third setpoint distance 820, the SIL 60 may be positioned closer to the surface W in an approach motion 825 to a fourth setpoint distance 830 of the gap 795. In an embodiment, the fourth setpoint distance 830 may be selected from the range of about 100 to 10 nanometers, e.g., about 50 to 10 nanometers, e.g., about 20-30 nanometers or about 30 nanometers. The fourth setpoint distance 830 may be the gap 795 at which the measurement is taken 835. During the measurement, the gap 795 is substantially maintained at the fourth setpoint distance 830.

Once the measurement is complete, the SIL 60 is positioned further away from the surface W to either enable a further measurement at another location on the surface or exchange of the surface W for another surface W. In an embodiment, the SIL 60 is positioned further away from the surface W in a retraction motion 840 to a third setpoint distance 820, which may have the same value as for the approach motion 825 or may be different therefrom. From the third setpoint distance 820, the SIL 60 is positioned further away from the surface W in a retraction motion 845 to a second setpoint distance 810, which may have the same value as for the approach motion 815 or may be different therefrom.

As noted above, the SIL 60 may be maintained at the second setpoint distance 810 to enable relatively safe relative movement 855 between the surface W and the SIL 60 to, e.g., horizontally position the SIL 60 over a further target 30 by relative movement between the SIL 60 and the target (e.g., moving the surface W horizontally and/or moving the SIL 60 horizontally). So, in an embodiment, for each target at a different location on the surface W, the approach motions 815 and 825 and retraction motions 840 and 845 of the SIL is repeated to help avoid damage of the surface W and the SIL 60 during relative motion between the SIL 60 and the surface W. In an embodiment, the retraction motions 840 and 845 may be combined into a single motion to the second setpoint distance 810, where, for example, the next operation is relative movement 855 between the surface W and the SIL 60 to position the SIL 60 over a further target 30.

If the surface W is being replaced with another surface W or the sensor is being shut down, the SIL 60 is positioned further away from the surface W in a motion 850 to a first setpoint distance 800, which may have the same value as for the start of the motion 805 or may be different therefrom. In an embodiment, the motions 840, 845 and 850 may be combined into a single motion to the first setpoint distance 800, where, for example, the next operation is the surface W being replaced with another surface W or the sensor being shut down.

In an embodiment, the approach motion 805 need not have the same parameters (e.g., acceleration, speed, setpoint, etc.) as the retraction motion 850. Similarly, in an embodiment, the retraction motion 845 need not have the same parameters (e.g., acceleration, speed, setpoint, etc.) as the approach motion 815. Similarly, in an embodiment, the retraction motion 840 need not have the same parameters (e.g., acceleration, speed, setpoint, etc.) as the approach motion 825.

These various motions take time due to, e.g., inertia of moving parts and limitations of the actuator and/or its amplifier. To improve productivity, it is desirable to reduce the time taken within the limits and constraints of the sensor system, the small distances, the control system bandwidth, etc. In particular, "extra" time in the motions 815, 825, 840 and 845 can significantly impact productivity (e.g., number of targets measured per minute).

In an embodiment, the approach velocity in motion 815 may be limiting for the productivity (as well as the approach velocity in motion 805, although the motion 805 occurs less frequently than the approach motion 815). For example, the GES may only be usable to the outer limit of a near-field gap distance (e.g., about 350 to 100 nanometers, e.g., about 300 nm), so the available "braking" distance before the SIL would impact the surface W is relatively short, e.g., a fraction of the about 350 to 125 nanometers, e.g., about 300 nm. So, given that "brake" distance and other conditions of the system, a maximum allowable approach velocity for motions 805 and 815 is determined, e.g., about 100-1000 m/s, e.g., 250-350 µm/s or about 300 µm/s. So, since the GES may not be usable outside a near-field gap distance, the relative motion between the SIL 60 and surface W would be with that maximum velocity over the full range from the first setpoint distance 800 at the start of each surface W and from the second setpoint distance 810 between targets on a surface W. So, it is desirable to enable a higher velocity at least in motion 815.

Accordingly, in an embodiment, there is provided a multi-step "braking" process. That is, in an embodiment, the relative motion between the SIL 60 and the surface W is "braked" in two or more steps. In a first step, a "far-field braking" is applied using a trigger signal in the range to the second setpoint distance 810 and/or to the third setpoint distance 820. At the third setpoint distance 820, a "near-field braking" is applied by the use of, e.g., the GES signal. With such an approach, the velocity in motion 805 and/or motion 815 can be increased by, e.g., a factor of about 10 times to, e.g., about 1-10 mm/s, e.g., 2.5 to 5 mm/s, e.g., about 3 mm/s. The new maximum allowable velocity may be determined by the brake distance needed due to inertia of the applicable components and by the power electronics (e.g., the brake distance may not exceed the range of the SIL stage). For example, the multi-step brake process may reduce the time for motion 815 by a factor of about 5 times.

In an embodiment, the trigger signal is an optical signal. In an embodiment, radiation 790 that propagates through the objective 15 and the SIL 60, and that is redirected by the surface W and returns through the objective 15 and the SIL 60, is used as the basis for the optical trigger signal. So, with such a signal, the impact on the overall system design is relatively small by using illumination that is already available for, e.g., other control signals, and by using a relatively simple detection method, which has a low impact on the optical path.

As noted above, in the approach and/or retraction motions, the distance between the SIL 60 and the surface W is changed between, for example, a distance between the SIL 60 and the surface W of the order of 1 mm and a distance between the SIL 60 and the surface W of several tens of nanometers. During this approach and/or retraction motion, the SIL 60 may be actively controlled such that the SIL tip 797 coincides with the focus position 798 of the objective 15.

As will be appreciated, the approach and/or retraction motions involve acceleration and deceleration. As such, without active damping of the SIL 60, this acceleration and deceleration may cause, for example, the SIL 60 to oscillate in, e.g., its flexible suspension relative to the objective 15. This oscillation may have a negative impact on the maximum allowable acceleration/deceleration, and hence on the maximum achievable velocity, at which the distance between the SIL 60 and the surface W can be changed. This may cause a throughput loss. The oscillations may also lead to loss of critical control signals for control of the SIL 60 and/or the objective 15 with respect to the surface W. Hence, it is desirable to reduce, for example, this SIL 60 oscillation by active damping or closed loop control of the position of the SIL 60 with respect to the focus of the objective 15. Thus, it is desirable to, for example, provide closed loop control of the position of the planar tip 797 of the SIL 60 with respect to the focus position 798 of the objective 15 and/or control of the objective 15 with respect to the planar tip 797 (whether, for example, to have the tip come closer to the focus position 798 and/or have the focus position 798 come closer to the tip, or to have the tip move away from the focus position 798 and/or have the focus position 798 move away from the tip). Accordingly, a suitable focus control signal is desired. Such a focus control signal should desirably not be disturbed by the surface W, which at some point will be close to the focus position of the objective 15.

Closed loop focus control of an optical element with respect to an object, or vice versa, based on a focus control signal can be done using any of a variety of position measurement techniques to provide the focus control signal. Such position measurement techniques may include optical position measurement techniques such as astigmatic focusing, spot size detection, Foucault knife edge detection, and/or bi-confocal detection.

These various optical position measurement techniques of focus control signals may share some common properties. For example, the focus control signal is often derived from an unbalance in radiation detected by two or more detectors (including separate detectors in the form of separate portions of single sensor), e.g., two or more photodiodes or camera sensors. The unbalance is often caused by an intentionally added wavefront aberration such as astigmatism, or by blocking a part of the beam (Foucault knife edge, bi-confocal detection) or by selecting only a part of the beam with a small or masked detector. The focus control signal is often normalized to the sum of the radiation signals detected by the various detectors to make the focus control signal less sensitive to reflectivity of the object onto which the optical element is focusing or to make the signal less sensitive to intensity variations of the source of the radiation. That is, by using a plurality of detectors, it may avoid directly comparing an amount of redirected measured radiation to a preset threshold, and with that, may avoid a direct dependence on, e.g., the reflectivity of the surface from which the radiation is redirected, which reflectivity can vary an order of magnitude, depending on the structures, materials, etc. present on the surface. So, working with a plurality of detectors, and evaluating their signals with respect to each other, helps make the system more robust against process variations.

Figure 9:
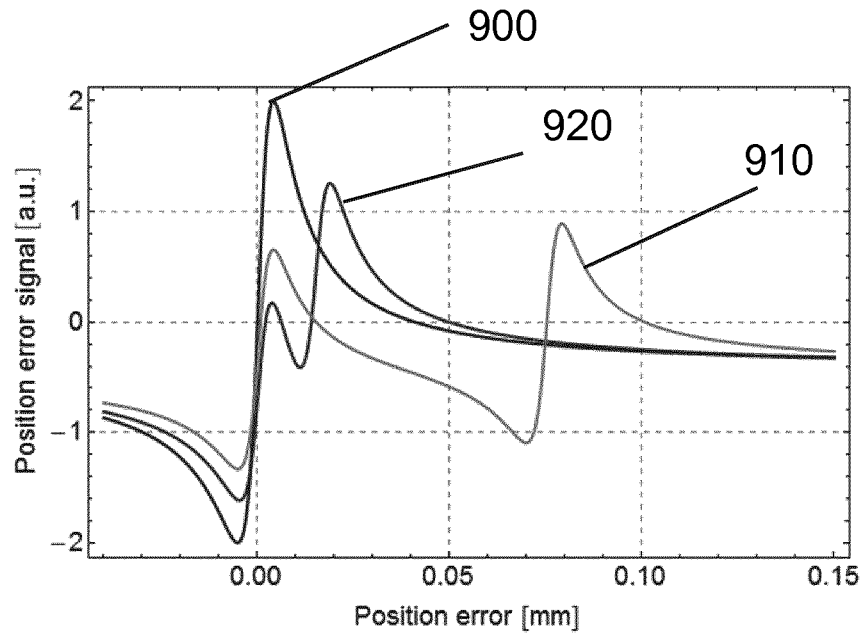
FIG. 9 depicts a graph of example calculated 'S-curve' focus control signals (of position error signal versus position error)

A focus control signal will typically resemble a 'S-curve' of positional error signal versus position error. An example of such a curve is curve 900 in FIG. 9, where the position error signal may be an arbitrary unit (as shown in FIG. 9) and the position error is in distance unit (e.g. millimeters as shown in FIG. 9). But, if, for example, the object onto which the optical element is focusing the radiation is a multilayer structure (e.g., a part of a patterned semiconductor substrate) with a thickness of at least the order of the focal depth then more than one interface between different layers will contribute to the detected signal. A conventional focus control signal cannot distinguish between different layers that are separated by a distance of the order of the focal depth.

So, in an embodiment, with a hyper-NA SIL system, radiation reflected by (F)TIR and Fresnel reflection at the SIL tip may be large enough to generate a 'S-curve' focus control signal (such as curve 900 in FIG. 9) by means of a conventional position measurement technique. That is, a position measurement technique for the position of the objective 15 with respect to the SIL tip 797 may take advantage of (frustrated) total internal reflection and Fresnel reflection at the interface of the SIL tip 797 with the external environment by measuring such reflected radiation to obtain a focus control signal.

But, a problem may arise with this approach when the SIL 60 comes close to the surface W. At a distance between the SIL 60 and the surface W smaller than a few tens of micrometers, at least two reflections may start to overlap on the detectors that detect the radiation. One reflection comes from the interface between the SIL 60 and the external environment (e.g., air) and another other reflection comes from the surface W.

Referring to FIG. 9, examples of calculated 'S-curve' focus control signals (of position error signal versus position error in this example) using an example conventional astigmatic focusing method and a particular optical configuration are depicted. Curve 900 is for a situation without a surface W near the SIL (and so shows a typical 'S-curve'). Curve 910 is for a situation with surface W at an example distance of about 75 μm from the SIL 60 tip. Curve 920 is for a situation with a surface W at an example distance of about 15 μm from the SIL 60 tip. So, for a situation with a surface W adjacent the SIL 60 and for distances between the SIL 60 and the surface W larger than or equal to about 75 μm, or larger than or equal to about 85 μm, or larger than or equal to about 95 μm, or larger than or equal to about 105 μm, or larger than or equal to about 115 μm, two separate generally well-behaved 'S-curves' will be generated for each of the two surfaces (i.e., the SIL 60 tip and the surface W) as shown in curve 910. But, for a distance smaller than the foregoing distances, but larger than the focal depth, the 'S-curve' focus control signal will be severely disturbed and may even have several zero-crossings and sign changes of the signal's slope as shown by curve 910. When the distance between the SIL 60 and the surface W is of the order of the focal depth, a single generally well-behaved 'S-curve' focus control signal is obtained again. However, when this occurs, the SIL 60 may no longer be controlled with respect to the objective 15, but instead with respect to the surface W using, for example, another control signal that is based on the evanescent coupling between the SIL 60 and the surface W.

So, the reflection by the surface W may severely disturb the position control signal for control of the relative position between the SIL 60 and the objective 15 in respect of the focus of the objective 15. Accordingly, a preventative measure should be taken.

In an embodiment, disturbance of the focus control signal is reduced, or substantially eliminated, by separating the reflections from the SIL 60 and the surface W by exploiting an optical property of TIR inside the SIL 60, which causes a linear polarized incident ray to become elliptically polarized upon reflection by TIR. The polarizations can be then be effectively separated by optical processing to create a focus control signal (e.g., a position control signal of the SIL 60 tip position with respect to the focus of the objective 15) that has low sensitivity (e.g., almost perfectly insensitive) to the reflection by the surface W for distances between the SIL 60 and the surface W larger than approximately half the wavelength of the position measurement beam.

The above mentioned optical effect is caused by a phase difference that is introduced between p- and s-polarized components of the incident ray electric field vector under conditions for TIR. This phase difference causes reflected radiation in parts of a pupil or back-focal plane (or a conjugate plane thereof) of the objective 15, to become elliptically polarized when linearly polarized radiation is directed toward the surface W. The p-polarized component (sometimes referred to as transverse-magnetic (TM) polarization) is polarized radiation with its electric field lying in the plane of incidence, while the s-polarized component (sometimes referred to as transverse-electric (TE) polarization) is polarized radiation with its electric field normal to the plane of incidence.

Figure 10:
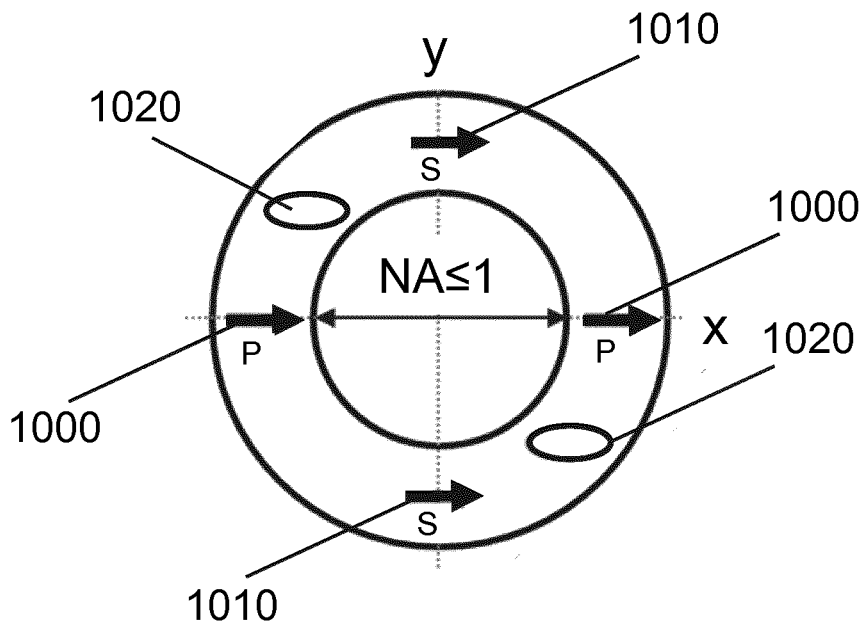
FIG. 10 schematically depicts a pupil or a back-focal plane (or a conjugate plane thereof) of a hyper-NA objective and various polarizations therein.

To illustrate this optical effect, reference is made to FIG. 10, which schematically depicts a pupil or back-focal plane (or a conjugate plane thereof) of a hyper-NA objective. The objective is illuminated with linearly polarized radiation with polarization along the X-axis (in this example). The rays focused and reflected in the XZ plane of the pupil or back-focal plane (or a conjugate plane thereof) are p-polarized 1000 before and after TIR. The rays focused and reflected in the YZ plane of the pupil or back-focal plane (or a conjugate plane thereof) are s-polarized 1010 before and after TIR. All other rays at NA>1 have both p- and s-components of polarization. That is, after reflection, these rays have elliptical polarization 1020 due to TIR.

Figure 11:
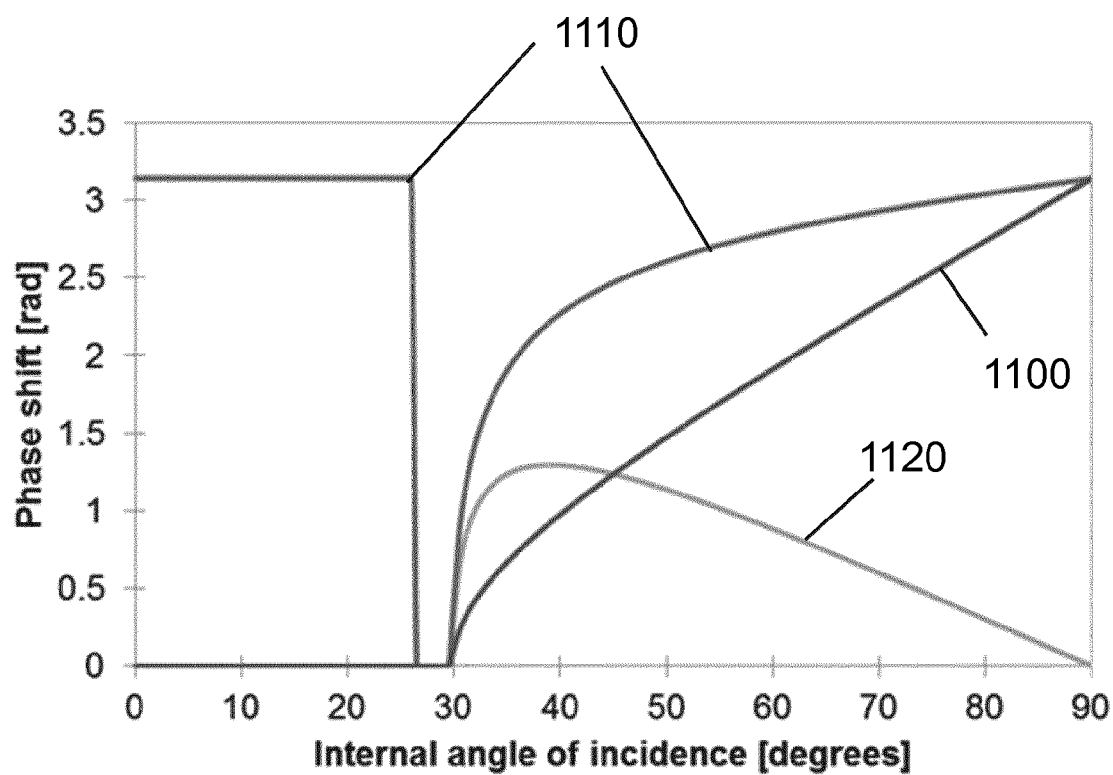
FIG. 11 depicts examples of calculated phase shift versus internal angle of incidence in a SIL due to total internal reflection of s-polarized radiation, p-polarized radiation, and the phase difference between the p- and s-polarized radiation.

So, referring to FIG. 11, examples of calculated phase shift versus internal angle of incidence in a SIL due to TIR of s-polarized radiation 1100, p-polarized radiation 1110, and the phase difference 1120 between the p- and s-polarized radiation for a SIL with refractive index n=2.01. The discontinuity at about 26 degrees internal angle of incidence is due to Brewster's angle. TIR occurs beyond about 30 degrees angle of incidence inside the SIL medium.

Thus, TIR causes a large fraction of the optical power to be reflected back into the pupil or back-focal plane (or a conjugate plane thereof) with a polarization that is perpendicular to that of the linearly polarized illumination radiation. Therefore, if the objective 15 is illuminated with linear polarized radiation with a polarization direction along, e.g., the x-axis, the optical power after TIR is split into a radiation intensity distribution in the $n_{SIL}$ sin α>1 (where the external environment has a refractive index of about 1) part of the pupil or back-focal plane (or a conjugate plane thereof), with its polarization along the x-axis and a radiation intensity distribution in the $n_{SIL}$ sin α>1 (where the external environment has a refractive index of about 1) part of the pupil or back-focal plane (or a conjugate plane thereof), with its polarization along the y-axis. The reflection from the surface W essentially maintains the polarization of the illumination and therefore contributes (mostly) to the radiation distribution in the $n_{SIL}$ sin α≤1 (where the external environment has a refractive index of about 1) part of the pupil or back-focal plane (or a conjugate plane thereof), with a polarization direction along the x-axis.

Figure 12A:
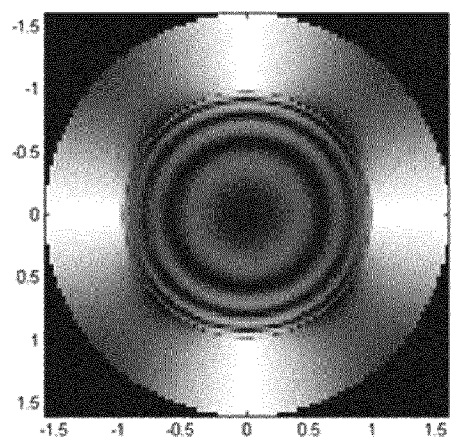
FIG. 12(A) depicts a simulated example of radiation intensity distribution of total internal reflection radiation from a SIL that is separated from a surface by more than a half a wavelength and that is illuminated with radiation linearly polarized in the horizontal direction, where the reflected radiation has been processed by a horizontal polarizer.
Figure 12B:
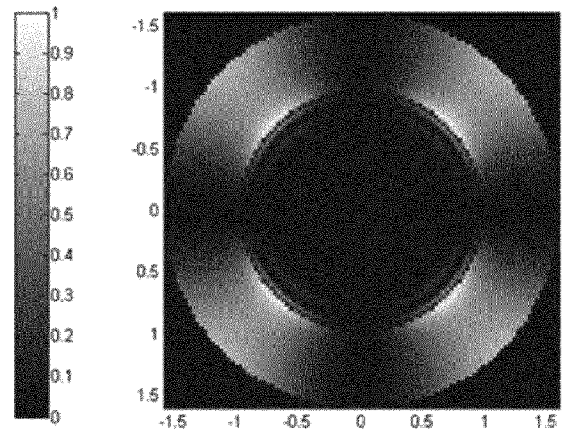
FIG. 12(B) depict a simulated example of radiation intensity distribution of total internal reflection radiation from a SIL that is separated from a surface by more than a half a wavelength and that is illuminated with radiation linearly polarized in the horizontal direction, where the reflected radiation has been processed by a vertical polarizer.

Simulated examples of such a radiation intensity distribution are shown in FIG. 12. The simulated radiation distributions in the pupil or back-focal plane (or a conjugate plane thereof), of FIG. 12 are of an NA=1.6 lens with radiation linearly polarized in the horizontal direction and having a wavelength of 660 nm, for a 1500 nm distance between the SIL 60 and surface W with a surface grating pattern. FIG. 12(A) shows the radiation distribution as "detected" in the pupil or back-focal plane (or a conjugate plane thereof), through a horizontal polarizer. The concentric fringes in the center are due to interference in the gap between the SIL 60 and the surface W. FIG. 12(B) shows the radiation distribution as "detected" in the pupil or back-focal plane (or a conjugate plane thereof), through a vertical polarizer. This fraction of the radiation has not had significant interaction with the surface W and is mainly due to TIR at the interface between the SIL 60 tip and the external environment.

Figure 13A:
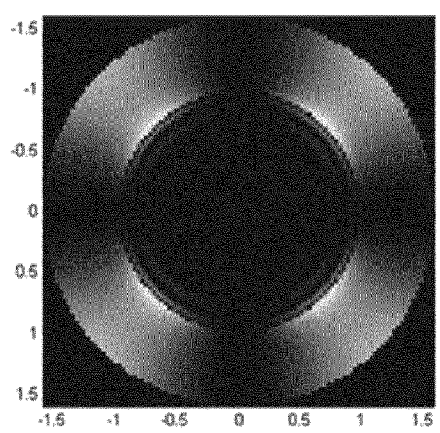
FIG. 13(A) depicts a simulated example of radiation intensity distribution of total internal reflection radiation from a SIL that is separated from a surface by more than a half a wavelength and that is illuminated with radiation linearly polarized in the vertical direction, where the reflected radiation has been processed by a horizontal polarizer.
Figure 13B:
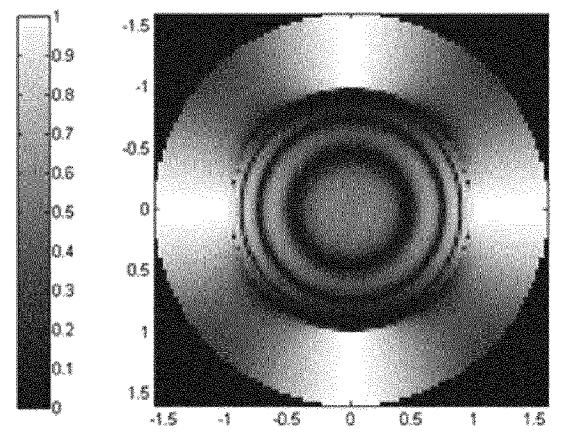
FIG. 13(B) depicts a simulated example of radiation intensity distribution of total internal reflection radiation from a SIL that is separated from a surface by more than a half a wavelength and that is illuminated with radiation linearly polarized in the vertical direction, where the reflected radiation has been processed by a vertical polarizer.

Further simulated examples of such a radiation intensity distribution are shown in FIG. 13. The simulated radiation distributions in the pupil or back-focal plane (or a conjugate plane thereof), of FIG. 13 are of an NA=1.6 lens with radiation linearly polarized in the vertical direction instead and having a wavelength of 660 nm, for a 1500 nm distance between the SIL 60 and surface W with a surface grating pattern. FIG. 13(A) shows the radiation distribution as "detected" in the pupil or back-focal plane (or a conjugate plane thereof), through a horizontal polarizer. This fraction of the radiation has not had significant interaction with the surface W and is mainly due to TIR at the interface between the SIL 60 tip and the external environment. FIG. 13(B) shows the radiation distribution as "detected" in the pupil or back-focal plane (or a conjugate plane thereof), through a vertical polarizer. The concentric fringes in the center are due to interference in the gap between the SIL 60 and the surface W.

So, from FIGS. 12 and 13, it can be seen that it is possible to effectively separate the reflection at the planar interface between the SIL 60 and the external environment (e.g., gas such as air) from the reflection at the surface W. This can be done by illuminating the objective 15 with linear polarized radiation, while detecting the reflected radiation through a polarizer that only propagates (e.g., transmits) the polarization state that is perpendicular to the linear polarization of the illumination. So, in an embodiment, a position control signal is obtained in a system and process that illuminates the objective 15 and SIL 60 with linear polarized illumination while detecting, with a detector, reflected radiation from the SIL 60 through a polarizer that only propagates (e.g., transmits) the polarization state that is perpendicular to the illumination to arrive at a focus control signal based on such measured radiation. The system and process may otherwise be a conventional focus control signal detection system and method. Thus, it is possible to detect a focus control signal 'S-curve' for the relative position between the SIL 60 and the objective 15 in respect to the focus of the objective 15 in a way that is essentially insensitive to the (position of the) surface W.

Figure 14:
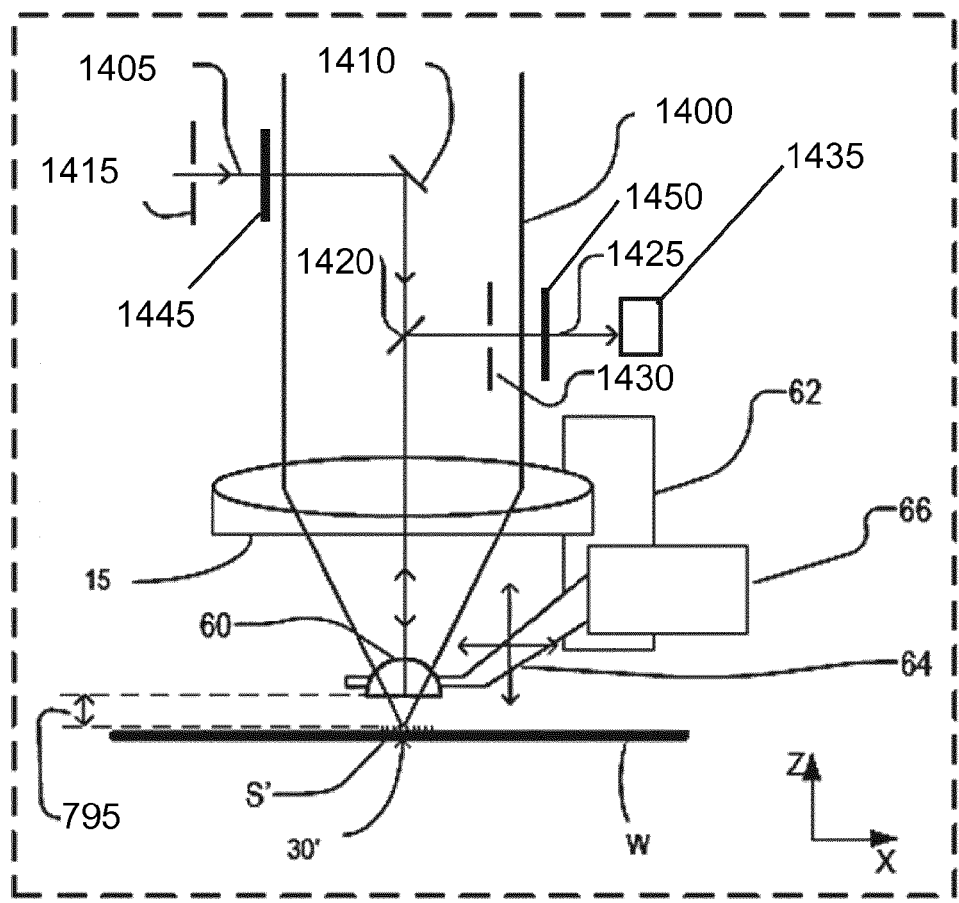
FIG. 14 is an enlarged detail of parts of the apparatus of FIG. 6 showing an embodiment of a focus position detection system.
Figure 15:
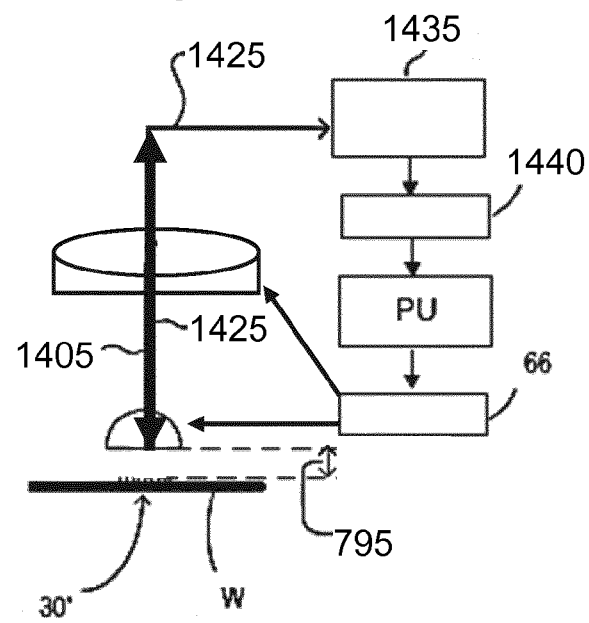
FIG. 15 illustrates schematically a focus position detection and control arrangement in the apparatus of FIG. 14.

FIG. 14 shows a schematic partial enlarged view of parts close to the target, in the embodiment apparatus of FIG. 6. FIG. 14 in particular provides a schematic view of example optical paths for use in determining the focus position of the objective 15 in the apparatus of FIG. 6 and control of positioning of the objective 15 and/or SIL 60 on the basis of that determination. FIG. 15 shows schematically an embodiment of a focus position determining and controlling system. With regard to the function of the apparatus as a metrology or inspection apparatus, a measurement illumination beam 1400 follows an illumination path comprising optical components 12 (not shown in FIG. 14 for convenience), 13 (not shown in FIG. 14 for convenience), 15, 16 (not shown in FIG. 14 for convenience), 17 (not shown in FIG. 14 for convenience), and 60 described above with reference to FIG. 6, and thus will not be discussed here. A collection path comprising optical components 60, 15 to collect radiation redirected by target 30' is also described above with reference to FIG. 6. The radiation collected by optical components of the collection path is directed to a detector 18 (not shown in FIG. 14 for convenience) connected to processor system PU (not shown in FIG. 14 for convenience) for target reconstruction or other purposes. As mentioned above, an example application of these parameters may be for determining overlay error or determining critical dimension (CD). Target 30' may be formed on a substrate W that has been patterned and processed using the lithographic apparatus of FIG. 1 and the cluster of processing tools described above with reference to FIG. 2. The technique disclosed in the present disclosure is not limited to such inspection apparatus. In another application, for example optical recording, illumination paths and collection paths may be similarly arranged.

In an embodiment, to determine the focus position of the objective 15 and control a relative position between the objective 15 and SIL 60, a radiation beam 1405 (e.g., a laser or broadband radiation beam) follows an optical path that will be referred to as the control path. Beam 1405 may be referred to as a control beam and may be beam 790 described herein, a beam to arrive at the GES, and/or other beam used to determine a distance or position. FIG. 14 shows an example ray of the beam 1405; in practice, beam 1405 will have a width and significantly fill the SIL 60. Thus, the beam 1405 will typically illuminate the tip of the SIL 60 with radiation at multiple angles at once (due to the refraction by the objective 15 and/or SIL 60), giving rise to a single focus at or near the tip of the SIL 60. This makes it possible to obtain the TIR ring of radiation in the pupil or back-focal plane (or a conjugate plane thereof) as shown in, e.g., FIGS. 10, 12 and 13.

The control path in this example comprises optical components 1410 and 1420, which may take the form of mirrors or partially-reflective surfaces. Control beam 1405 is directed to SIL 60 by optical component 1410 through optical component 1420. Control beam 1405 passes through objective 15 and SIL 60 to impinge at an interface of the tip of SIL 60 and the external environment (e.g., gas such as air), where desirably the focus of objective 15 is located during an approach and/or retraction motion. The control beam radiation redirected by, e.g., surface W and/or the interface of the tip of SIL 60 and the external environment, is labeled 1425 and is directed by optical component 1420 to a detector arrangement 1435 (e.g., comprising a plurality of detectors, such as a plurality of sensors, e.g., photodiodes or camera sensors). As noted above, radiation incident at the interface of the tip of SIL 60 and the external environment at an angle higher than a critical angle for the interface will reflect back to the detector arrangement 1435 and thus can give a measure of the focus position of the objective 15. That is, radiation reflected back due to (frustrated) total internal reflection and Fresnel reflection at the interface can be measured using the detector arrangement 1435 to arrive at a focus control signal.

But, as discussed above, the surface W is relatively close to the SIL 60 and so radiation can pass to the surface W and thus the radiation received at the detector arrangement may comprise radiation arising from reflection by the surface W in addition to the interface. So, to arrive at a measure of the focus position of the objective 15 in such a situation, the objective 15 is illuminated with linear polarized radiation. A polarization device 1445, such as a polarizer, may be used to provide the linear polarized radiation, where, e.g., the source of radiation 1405 does not provide linear polarized radiation. Polarization device 1445 may be omitted if the source of radiation 1405 provides linear polarized radiation. Polarization device 1445 may be located at a different position to provide linear polarized radiation to SIL 60.

As discussed above, TIR at the interface of the tip of SIL 60 and the external environment causes a polarization change. Accordingly, the redirected radiation from the interface of the tip of SIL 60 and the surface W is passed through a polarization device that only propagates (e.g., transmits) the polarization that is perpendicular to the linear polarization of the illumination. To do so, a polarization device 1450 (such as a horizontal polarizer, vertical polarizer or a polarizing beam splitter) is provided to block the polarization of the linearly polarized illumination and to allow the polarization that is perpendicular to the linear polarization of the illumination to propagate (e.g., transmit) toward detection arrangement 1435. The redirected radiation propagating from polarization device 1450 is then measured by the detection arrangement 1435. Polarization device 1450 may be located at a different position to provide redirected radiation with its polarization perpendicular to the linear polarization of the illumination at detection arrangement 1435. Polarization device 1450 thus effectively enables separation of the reflection at the interface between the SIL 60 and the external environment (e.g., gas such as air) from the reflection at the surface W.

So, in an embodiment, a position control signal is obtained in a system and process that illuminates the objective 15 and SIL 60 with linear polarized illumination while detecting, with a detector arrangement 1435, reflected radiation from the SIL 60 through a polarization device 1450 that only propagates (e.g., transmits) the polarization state that is perpendicular to the illumination. The redirected radiation propagated (e.g., transmitted) from polarization device 1450 is measured to arrive at a focus control signal, which can then be used in a control loop to control the position of the objective 15 and/or SIL 60 to enable control of, e.g., the focus position of the objective 15 at the tip of the SIL 60. Thus, it is possible to detect a focus control signal 'S-curve' for the positioning of the objective 15 and/or SIL 60 to enable control of, e.g., the focus position of the objective 15 at the tip of the SIL 60.

In an embodiment, an aperture 1415 may be placed in the control path to reduce the width of the control beam 1405. An aperture stop 1430 may also be placed in the control path to select a portion of radiation 1425 that is delivered to the detection arrangement.

For convenience of description, the source to generate control beam 1405 is not shown in FIG. 14. A radiation source emitting radiation of one or more wavelengths selected from the ranging of 100 to 900 nm may be used. The source may be, for example, a lamp emitting white light or a so-called white light laser. In other embodiments, the radiation may be polychromatic (comprising many individual wavelengths), rather than having a continuous broad spectrum. In an embodiment, the radiation may be substantially monochromatic (comprising a narrowband optical line spectrum), rather than having a continuous broad spectrum. The source of the measurement illumination beam 1400 and control beam 1405 may be one and the same. In one such embodiment the laser source 70 of FIG. 6 may be replaced by a broadband light source to supply radiation for both beams 1400 and 1405, when the application does not require the use of a highly coherent light source. Alternatively, different sources may be used to generate beams 1400 and 1405.

FIG. 15 illustrates schematically an arrangement to monitor the focus position of the objective 15 and enable control in respect of the focus position. The arrangement of FIG. 15 includes a detector arrangement 1435 (e.g., such as described above). Radiation 1425 is directed to detector arrangement 1435. The one or more signals produced by detector arrangement 1435 are directed to processor system 1440 which communicates with a processor system PU. Processor system 1440 processes the one or more signals produced by the detector arrangement to produce, e.g., a focus control signal as described herein and/or one or more setpoints for movement of a component. In an embodiment, such analysis may be performed by processor system PU. Processor system PU then uses the results of the determination to control the position of the SIL 60 and/or the objective 15 to a desired set point by activating one or more actuators (e.g., actuator 66). In this way, position control of the objective 15 and/or SIL 60 may be achieved to enable control of, e.g., the focus position of the objective 15 at the tip of the SIL 60.

Figure 16:
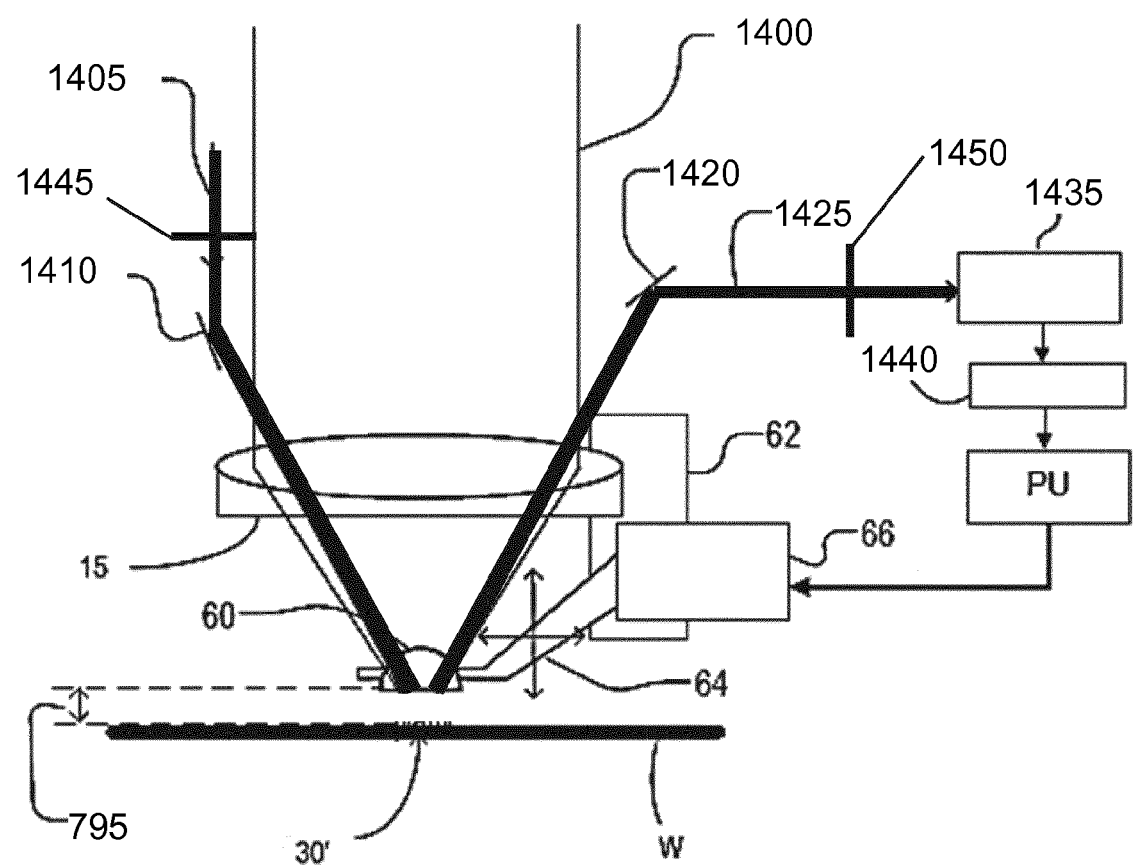
FIG. 16 is an enlarged detail of parts of the apparatus of FIG. 6 showing a further embodiment of a focus position detection system.

In an embodiment, SIL 60 may be irradiated obliquely by control beam 1405 at an incident angle different from zero. The optical arrangement of FIG. 14 to illuminate the target and collect the radiation emitted by the target as well as the control path may be adapted accordingly. An example of irradiating SIL 60 obliquely by a control beam 1405 is schematically illustrated in FIG. 16. SIL 60 is irradiated obliquely to the optical axis of SIL 60 by radiation 1405 via optical component 1410. Redirected radiation 1425 is directed to a detection arrangement as described herein.

In an embodiment, a plurality of measurement beams for gap control may be used. For example, there may be a plurality of beams provided, for example, according to the arrangement of FIGS. 14 and 15. There may be a plurality of beams provided, for example, according to the arrangement of FIG. 16. Or, there may be provided a combination of one or more beams provided, for example, according to the arrangement of FIGS. 14 and 15, and one or more beams provided, for example, according to the arrangement of FIG. 16.

Figure 17A:
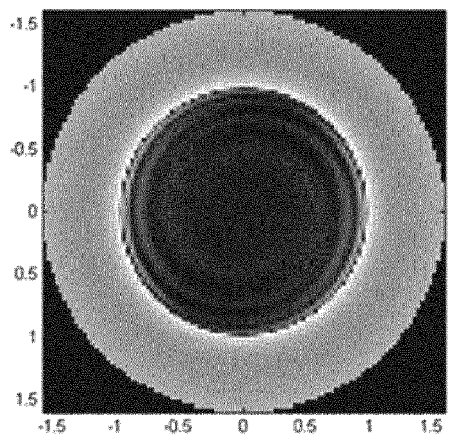
FIG. 17(A) depicts a simulated example of radiation intensity distribution of total internal reflection radiation from a SIL that is separated from a surface by more than a half a wavelength and that is illuminated with left-handed circularly polarized radiation, where the reflected radiation has been processed by a quarter-wave plate and a horizontal polarizer.
Figure 17B:
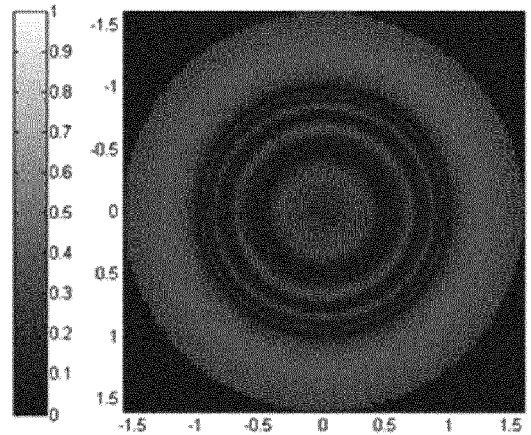
FIG. 17(B) depict a simulated example of radiation intensity distribution of total internal reflection radiation from a SIL that is separated from a surface by more than a half a wavelength and that is illuminated with left-handed circularly polarized radiation, where the reflected radiation has been processed by a quarter-wave plate and a vertical polarizer.

While use of linearly polarization has been discussed above for obtaining a control signal, it may be desirable to use circular polarized illumination for the detection of a control signals. So, simulated examples of a radiation intensity distribution in the pupil or back-focal plane (or a conjugate plane thereof), of the objective 15 of a hyper-NA optical arrangement illuminated with circularly polarized radiation are shown in FIG. 17. The simulated radiation distributions in the pupil or back-focal plane (or a conjugate plane thereof) of FIG. 17 are of an NA=1.6 lens with left-handed circularly polarized radiation having a wavelength of 660 nm, for a 1500 nm distance between the SIL 60 and surface W with a surface grating pattern. FIG. 17(A) shows the radiation distribution as "detected" in the pupil or back-focal plane (or a conjugate plane thereof), through a horizontal polarizer. The concentric fringes in the center are due to interference in the gap between the SIL 60 and the surface W. FIG. 17(B) shows the radiation distribution as "detected" in the pupil or back-focal plane (or a conjugate plane thereof), through a vertical polarizer. The concentric fringes in the center are due to interference in the gap between the SIL 60 and the surface W.

Figure 18A:
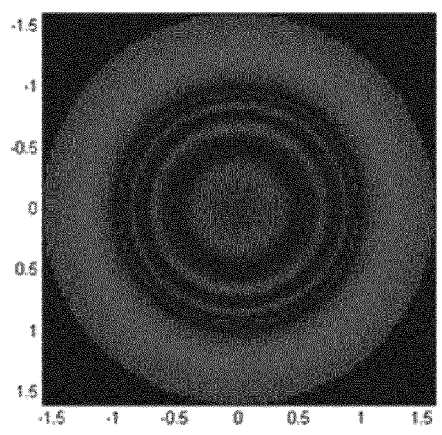
FIG. 18(A) depicts a simulated example of radiation intensity distribution of total internal reflection radiation from a SIL that is separated from a surface by more than a half a wavelength and that is illuminated with right-handed circularly polarized radiation, where the reflected radiation has been processed by a quarter-wave plate and a horizontal polarizer.
Figure 18B:
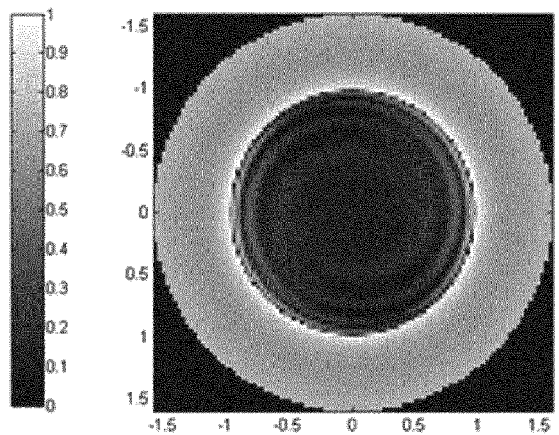
FIG. 18(B) depict a simulated example of radiation intensity distribution of total internal reflection radiation from a SIL that is separated from a surface by more than a half a wavelength and that is illuminated with right-handed circularly polarized radiation, where the reflected radiation has been processed by a quarter-wave plate and a vertical polarizer.

Further simulated examples of such a radiation intensity distribution with circularly polarized illumination radiation are shown in FIG. 18. The simulated radiation distributions in the pupil or back-focal plane (or a conjugate plane thereof), of FIG. 18 are of an NA=1.6 lens with right-handed circularly polarized radiation instead having a wavelength of 660 nm, for a 1500 nm distance between the SIL 60 and surface W with a surface grating pattern. FIG. 18(A) shows the radiation distribution as "detected" in the pupil or back-focal plane (or a conjugate plane thereof), through a horizontal polarizer. The concentric fringes in the center are due to interference in the gap between the SIL 60 and the surface W. FIG. 18(B) shows the radiation distribution as "detected" in the pupil or back-focal plane (or a conjugate plane thereof), through a vertical polarizer. The concentric fringes in the center are due to interference in the gap between the SIL 60 and the surface W.

From FIGS. 17 and 18, concentric fringes are observed, in all polarization permutations, due to interference between radiation reflected at the interface between the SIL 60 and the external environment and radiation reflected by the surface W. So, none of these polarization permutations appears to be inherently insensitive to the surface W. However, at the relevant distance range for the SIL position control problem as described herein, the outer parts of the pupil or back-focal plane (or a conjugate plane thereof), contain radiation that was reflected by total internal reflection at the interface between the SIL 60 and the external environment. Only at distances smaller than half the wavelength will this radiation interact with the surface W, at which point another evanescent coupling-based control signal may be used to control the gap distance between the SIL 60 and the surface W.

So, in an embodiment, substantially all radiation that is focused below the critical angle $n_{SIL} \sin \alpha = 1$ (where the external environment has a refractive index of about 1) is removed or reduced from the reflected radiation so that only or mostly radiation focused with an angle greater than the critical angle $n_{SIL} \sin \alpha = 1$ (where the external environment has a refractive index of about 1) is measured and used to arrive at a focus control signal. The radiation with an angle greater than the critical angle $n_{SIL} \sin \alpha = 1$ (where the external environment has a refractive index of about 1) is due to total internal reflection at the interface of the SIL and the external environment and thus can be used to provide a position control signal that enables control of the positioning of the SIL 60 and/or objective 15 such that, e.g., the focus of the objective 15 is at the tip of the SIL 60 and that is essentially insensitive to the (position of) the surface W.

Figure 19:
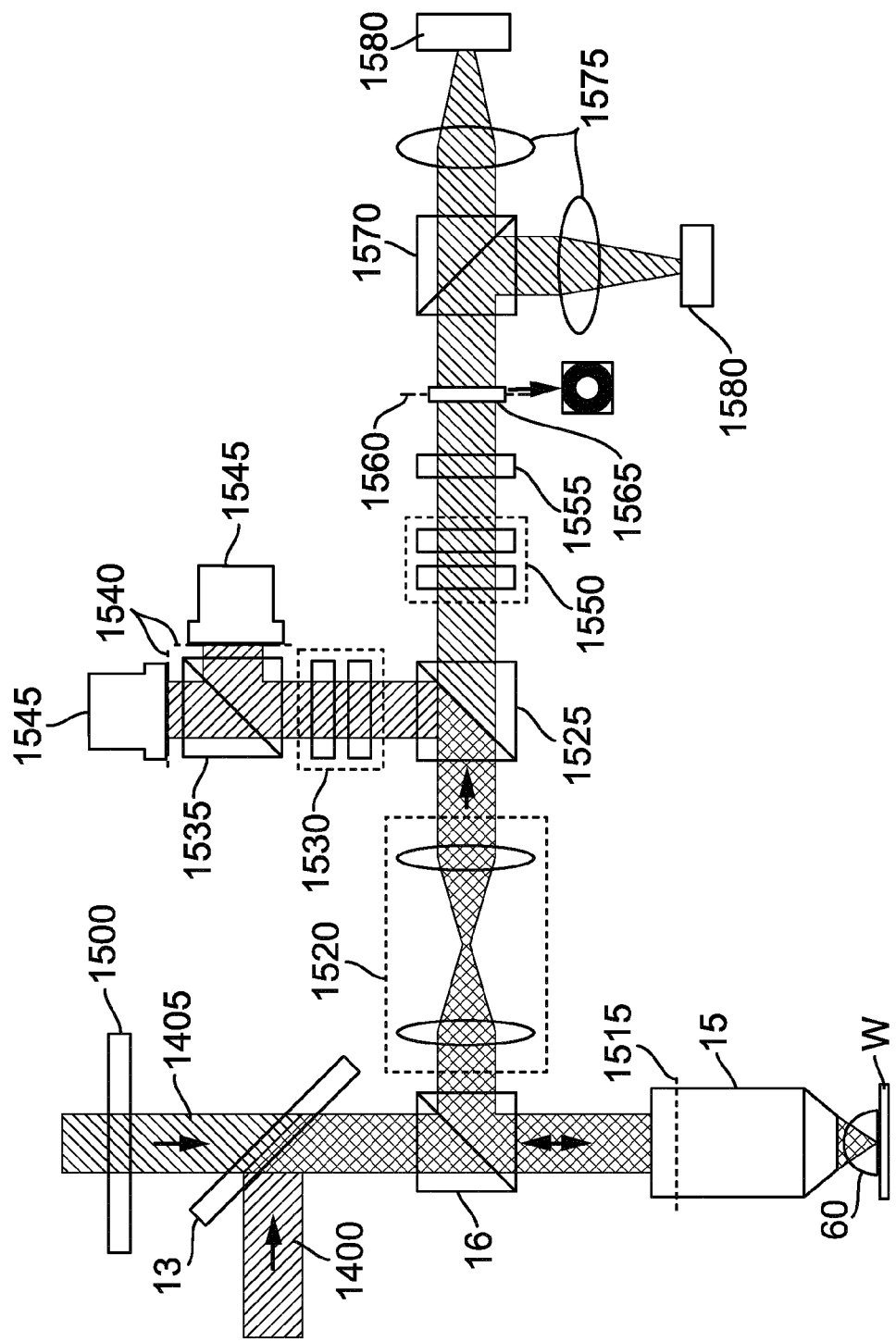
FIG. 19 is a detail of parts of the apparatus of FIG. 6 showing an embodiment of a focus position detection system.

FIG. 19 shows a schematic partial enlarged view of part of the embodiment apparatus of FIG. 6. FIG. 19 in particular provides a schematic view of example optical paths for use in determining the focus position of the objective 15 in the apparatus of FIG. 6 and enabling control in respect of the focus position. With regard to the function of the apparatus as a metrology or inspection apparatus, a measurement illumination beam 1400 may follow an illumination path comprising optical components 13, 16 (which in this example may be a non-polarizing beamsplitter), 15 and 60 described above with reference to FIG. 6, and thus will not be discussed here. Additionally, the illumination path of measurement illumination beam 1400 may comprises optical components 12 and 17 (both not shown in FIG. 19 for convenience) described above with reference to FIG. 6, and thus will not be discussed here. A collection path comprising optical components 60, 15 to collect radiation 1400 redirected by target is also described above with reference to FIG. 6.

In this embodiment, the collected radiation 1400 is directed by the optical component 16 to a relay system 1520 which directs the collected radiation 1400 to optical component 1525 (which in this example may be a non-polarizing beamsplitter). Collected radiation 1400 from optical component 1525 then passes via one or more bandpass and/or notch filters 1530 to optical component 1535 (which in this example may be a polarizing beamsplitter). The optical component 1535 provides the collected radiation 1400 to a detector arrangement 1545 connected to processor system PU (not shown in FIG. 14 for convenience) for target reconstruction or other purposes. In this example, the detector arrangement 1545 comprises a plurality of sensors with their measurement surfaces at or near a conjugate plane 1540 of the pupil plane 1515 of the objective 15. As mentioned above, an example application of these parameters may be for determining overlay error or determining critical dimension (CD). The target may be formed on a substrate W that has been patterned and processed using the lithographic apparatus of FIG. 1 and the cluster of processing tools described above with reference to FIG. 2. The technique disclosed in the present disclosure is not limited to such inspection apparatus. In another application, for example optical recording, illumination paths and collection paths may be similarly arranged.

In an embodiment, to determine the focus position of the objective 15 (and thereby enable control in respect of the focus position), a radiation beam 1405 (e.g., a broadband radiation beam) follows an optical path that will be referred to as the control path. Beam 1405 may be referred to as a control beam and may be beam 790 described herein, a beam to arrive at the GES, and/or other beam used to determine a distance or position. The control path in this example shares a number of optical components of the measurement or inspection radiation beam 1400, such as filter 13, optical component 16, relay system 1520 and optical component 1525, although it need not do so.

As shown in FIG. 19, control beam 1405 is directed to objective 15 and SIL 60 (via filter 13 and optical component 16 in this example). Control beam 1405 may comprise a narrow beam of broadband radiation that passes through objective 15 and SIL 60 to impinge at an interface of the tip of SIL 60 and the external environment (e.g., gas such as air), where desirably the focus of objective 15 is located during an approach and/or retraction motion. As discussed above, the beam 1405 may have a certain polarization. The polarization may be provided by polarization device 1500, where the source of beam 1405 does not provide the desired polarization. In an embodiment, the polarization provided to the objective 15 and SIL 60 may be circularly polarized illumination. Circularly polarized illumination may be obtained using a quarter wave plate 1500 (which may be placed close to the back focal plane of the objective 15). Linearly polarized radiation (which can come from the source of radiation 1405 or be provided by a polarization element, e.g., provided part of, or near, polarization device 1500) can be propagated (e.g., transmitted) via the quarter wave plate 1500 to become circularly polarized. Where the quarter wave plate 1500 is, e.g., close to the back focal plane of the objective 15, the reflected radiation 1405 may be reflected back through the objective 15 and via the quarter wave plate 1500 towards the detection arrangement for the radiation 1405. In an embodiment, a separate quarter wave plate 1555 may be provided to propagate (e.g., transmit) the collected radiation 1405 toward the detection arrangement. In an embodiment, horizontal polarized radiation is incident on the quarter wave plate 1500 so that left-handed circularly polarized radiation is provided to objective 15. In an embodiment, vertical polarized radiation is incident on the quarter wave plate 1500 so that right-handed circularly polarized radiation is provided to the objective 15.

The control beam radiation redirected by, e.g., surface W and/or the interface of the tip of SIL 60 and the external environment is directed by optical component 16 toward a detector arrangement 1580 (e.g., comprising a plurality of detectors, such as a plurality of sensors). In particular, in an embodiment, the reflected beam 1405 is collected by the SIL 60 and objective 15 and directed via one or more optical components to one or more bandpass and/or notch filters 1550. From the filter 1550, the collected beam 1405 is directed toward an optional polarization device 1555 (e.g., a quarter wave plate). Collected radiation 1405 then passes to optical component 1570 (which in this example may be a polarizing beamsplitter). The optical component 1570 provides the collected radiation 1405 via one or more lenses 1575 to a detector arrangement 1580 connected to processor system PU (not shown in FIG. 14 for convenience) to obtain a control signal for focus position control, or for other purposes. In this example, the detector arrangement 1580 comprises a plurality of sensors. The detector arrangement 1580 may be a conventional focus control signal detection method to generate a 'S-curve' as described herein. Each of the sensors of detector arrangement 1580 detect radiation with polarizations orthogonal to each other. The radiation used for control purposes, can be horizontal, vertical, right-hand circularly polarized or left-hand circularly polarized as it is incident on the pupil plane of the objective 15.

As noted above, in an embodiment, substantially all radiation that is focused below the critical angle $n_{SIL} \sin \alpha = 1$ (where the external environment has a refractive index of about 1) is removed or reduced from the reflected radiation so that only or mostly radiation focused with an angle greater than the critical angle $n_{SIL} \sin \alpha = 1$ (where the external environment has a refractive index of about 1) is measured and used to arrive at a focus control signal. To realize this, in an embodiment, a device 1565 is placed in a conjugate plane 1560 of the back focal plane or pupil plane 1515 of the objective 15 to remove or reduce radiation that is focused below the critical angle $n_{SIL} \sin \alpha = 1$ (where the external environment has a refractive index of about 1) from the reflected radiation. In an embodiment, device 1565 may comprise a mask arranged to block substantially all radiation that was focused below the critical angle $n_{SIL} \sin \alpha = 1$ (where the external environment has a refractive index of about 1). In an embodiment, the mask 1565 blocks all the incident radiation except for radiation that fits within a part left transmissive. As shown in FIG. 19, the mask 1565 may be in the form of a disk located at the center of the collected radiation beam 1405 with an appropriate dimension to block radiation focused with an angle smaller than the critical angle $n_{SIL} \sin \alpha = 1$ (where the external environment has a refractive index of about 1). In an embodiment, the blocking part or transmissive part of mask 1565 may have different radii or widths. In an embodiment, mask 1565 may comprise a plate with a transmissive ring opening (e.g., an annulus such as an annulus open aperture) around a central portion of the plate. In an embodiment, mask 1565 may be located at another position in the optical path from the SIL 60 to the detector arrangement 1580. In an embodiment, the mask 1565 may be connected to an actuator to move the mask 1565 in and out of the optical path. In an embodiment, there may be a plurality of masks 1565 of different design (e.g., different SILs, etc.), which may be placed into the optical path as needed. In an embodiment, the mask 1565 may define a configurable and variable blocking region. For example, the mask 1565 may be a shutter-type device, a LCD device, etc. In an embodiment, different mechanisms may be used for device 1565 to remove or reduce radiation that is focused below the critical angle $n_{SIL} \sin \alpha = 1$ (where the external environment has a refractive index of about 1) from the reflected radiation. For example, device 1565 may comprise a mirror with an aperture wherein the reflective portion around the aperture reflects a part of the reflected radiation to the detector arrangement 1580. As a further example, device 1565 may comprises a lens that amplifies an outer portion of the reflected radiation or shrinks a central portion of the reflected radiation.

Figure 20:
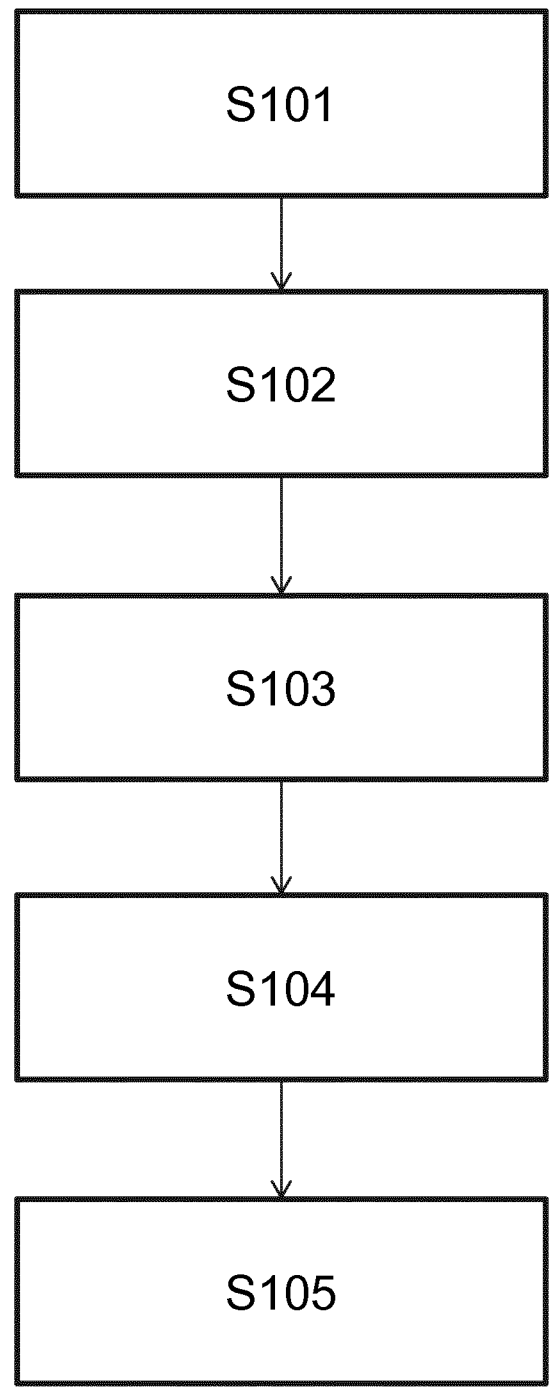
FIG. 20 is a schematic flow chart of an embodiment of a method.

FIG. 20 is a flow chart showing an example method of determining a focus position between components in an optical apparatus and enabling control in respect of the focus position. The method in general is implemented by optical and electronic hardware components, in combination with suitable programming instructions provided to a processing system. The focus position may be, e.g., a focus position of an optical element with respect to another optical element in a high numerical aperture optical arrangement. The high numerical aperture optical arrangement may be, for instance, the optical arrangement comprising objective 15 and SIL 60 where the SIL is close to a reflective or diffractive surface, such as target 30 or 30'.

The method comprises the following steps:

S101: A substrate comprising a target structure, such as a metrology target, is positioned, at a predefined position in the X-Y-Z directions, relative to the optical arrangement. A 'coarse' positioning (with an accuracy of the order of mm or microns) of the substrate surface relative to the high numerical aperture optical arrangement may be performed using other sensors, if necessary to set the gap value for use with, e.g., one or more radiation beams for finer control. Conventional substrate supports and positioning systems can be used for this step. A 'fine' positioning controls the gap.

S102: One or more radiation measurement beams are directed through the optical arrangement toward the target surface.

S103: The radiation redirected by an interface between an optical element or object (such as SIL 60) and its external environment, and optionally also the radiation redirected by the target surface, is collected by the optical arrangement and directed to one or more detector arrangements, such as described above. The detector arrangement(s) produces one or more detection signals based on the radiation received.

S104: A processing system analyzes the one or more detection signals and provides, e.g., a focus control signal as described herein and/or one or more setpoints for movement of a component. The processing system may further store the analysis output. Steps S102-S104 may be repeated as long as focus position control using the measurement beam(s) is needed. For example, in an embodiment, the detected redirected radiation from the interface may be used to produce a position error signal for the focus position of the objective 15 relative to the tip of the SIL 60 based on which the relative position of the objective 15 and SIL 60 is controlled.

In an embodiment, S102, S103 and S104 may comprise focusing radiation by an optical component into an object toward an interface of the object with an external environment; reflecting, at the interface, focused radiation by total internal reflection; detecting reflected radiation; and producing a position signal representative of the relative position between the focus of the optical component and the object based on the detected reflected radiation. In an embodiment, S102, S103 and S104 may comprise providing radiation that is linearly polarized in a first direction by an optical component into an object toward an interface of the object with an external environment; detecting radiation elliptically polarized or linearly polarized in a second direction different from the first direction arising from the reflection of the linearly polarized in the first direction at the interface; and producing a position signal representative of the position of the object and/or the component based on the detected reflected radiation elliptically polarized or linearly polarized in the second direction. In an embodiment, S102, S103 and S104 may comprise providing incident radiation by an optical component into a solid immersion lens toward an interface of the solid immersion lens with an external environment, wherein a surface is provided adjacent the interface and separated by a gap from the interface; processing reflected radiation arising from the reflection of the incident radiation at the interface and at the surface to reduce a proportion of radiation reflected from the interface in the reflected radiation; and producing a position signal representative of a position of the object and/or the component based on the processed radiation. In an embodiment, S102, S103 and S104 may comprise providing radiation that is circularly polarized by an optical component into an object toward an interface of the object with an external environment; and producing a position signal representative of a position of the object and/or objective based substantially only on radiation reflected from the interface arising from radiation incident at the interface at angles greater than a critical angle associated with the interface.

S105: Positioning in respect of the focus position is controlled using, or based on, an output of step S104. For example, a focus control signal may be compared to a set value, and processor system PU may then issue commands to cause change in the relative position between one or more parts of the optical arrangement, such as between an objective and SIL. In the example of the inspection apparatus of FIG. 6, the relative position between the objective 15 and SIL 60 may be adjusted using actuator 66. The set value should be such that there is sufficient time to respond with or during relative motion between the objective 15 and the SIL 60 or between the focus of the objective 15 and the SIL 60.

Thus, in an embodiment, there is provided detection or production of a position signal for the relative positioning between the SIL 60 and the objective 15 in respect of the focus of the objective 15 by means of total internal reflection in the SIL 60.

Further, in an embodiment, there is provided closed loop control of the relative position between the SIL 60 and objective 15 based on this signal as, for example, a method for active damping of the SIL 60 and/or objective 15 in respect of the focus of the objective 15 and/or for suppressing an external disturbance acting on the objective 15 and/or SIL 60. In particular, this control may be used while the objective 15 is being accelerated, decelerated, disturbed by other external forces, etc.

In an embodiment, there is provided a reduction of the negative impact on a position signal for the SIL 60 or objective 15 (e.g., a relative position between the SIL 60 and objective 15 or the focus of the objective 15 with respect to the SIL 60) due to radiation reflected from the surface W. In an embodiment, this reduction is achieved by detecting or producing the position signal from the fraction of the reflected radiation that has a polarization perpendicular to that of the illumination of the objective 15 (e.g., by using a polarizer that substantially only propagates radiation that has the polarization perpendicular to that of the illumination), which radiation that has a polarization perpendicular to that of the illumination arises at the reflection occurring at the interface of the SIL 60 with its external environment. A variety of known optical detection implementations can be used to arrive at the position signal from this particular polarization in the reflected beam. Thus, effectively the reflections at the interface of the SIL 60 with its external environment can be separated from reflections at the surface W through polarization sensitive detection. So, in an embodiment of such a configuration, no, or a vanishingly small, signal will be detected with conventional NA 1 lenses, however with a NA>1 SIL 60 there is a strong signal.

In an embodiment, there is provided a reduction of the negative impact on a position signal for the SIL 60 or objective 15 (e.g., a relative position between the SIL 60 and objective 15 or the focus of the objective 15 with respect to the SIL 60) due to radiation reflected from the surface W when the objective 15 is illuminated with circularly polarized radiation. In this case the reduction is achieved by blocking the reflected radiation that was focused below the critical angle $n_{SIL} \sin \alpha = 1$ while detecting or producing the position signal from the remainder of the radiation using, for example, a known optical detection method. Thus, effectively the reflections at the interface of the SIL 60 with its external environment can be separated from reflections at the surface W through a mask.

So, in an embodiment, method described herein for detecting or producing a position control signal for the SIL 60 or objective 15 (e.g., a relative position between the SIL 60 and objective 15 or the focus of the objective 15 with respect to the SIL 60) reduce a negative impact on the position signal by radiation reflected from the surface W located at a distance of the SIL 60 to the surface W larger than half the wavelength of the radiation used to generate the control signal.

In an embodiment, the methods are able to use the already available optical path between the objective 15, SIL 60, and surface W. Components that are added can be provided in less critical volumes, such as above the objective 15. Thus, in an embodiment, there is provided a focus control signal that operates through the objective 15 and SIL 60 (which are already used for metrology/inspection), and that can be obtained by an already available illumination source, and so may minimize the added complexity to the optical system. By operating through the SIL 60, the measurement of the focus position of the objective 15 with respect to the SIL 60 is performed directly using the SIL 60 and the objective 15.

In an embodiment, the control signal enables active damping between the SIL 60 and the objective 15 and/or suppression of an external disturbance acting on the SIL 60 and/or objective 15, which can enable: (i) a higher throughput with faster motion and/or (ii) lower disturbance on one or more other control signals that assume the SIL 60 is in focus with respect to the objective 15.

In an embodiment, there is provided a method and system that is robust to process variations (e.g. different reflection coefficients from different surfaces) because, in an embodiment, signals from at least two detectors are processed together, and so no absolute signal may be required.

In an embodiment, there is provided a method and system that (i) provides polarized radiation via objective 15 at the interface of a SIL 60 and an external environment, (ii) filters polarization of radiation reflected from the interface and a surface W adjacent the SIL 60, and (iii) obtains a position signal from the difference in phase shifts of the radiation reflected at the interface (due to total internal reflection) and at the surface W. Thus, a position signal related to the SIL 60 and/or objective 15 is obtained by separating the reflection from the interface and the reflection from the surface W by exploiting a phase shift between s and p polarized radiation arising from total internal reflection at the interface.

In an embodiment, there is provided a method and system that focuses radiation with a known first polarization state into a SIL 60 adjacent a surface W. The radiation reflected by total internal reflection inside the SIL 60 at its interface with the external environment is substantially polarization mixed, i.e., comprising radiation of the first polarization state and comprising radiation of a second orthogonal polarization state. The radiation reflected from the surface W will be mostly unchanged from the first polarization state, due to the relative small angle of incidence. Then, by detecting light in second polarization state, a position signal (e.g., focus error signal) can be obtained that is representative of the SIL 60 because the radiation that is reflected from the interface of the SIL 60 is effectively separated from the radiation that is reflected from the surface W. In this way, cross-talk in the position signal between radiation reflected from the SIL and from the surface W that would otherwise occur if the first polarization state were detected is avoided. The position signal may be a S-curve as described above that can be used to determine the relative position between the SIL 60 and the objective 15.

While embodiments herein have been discussed mostly in relation to an approach and/or retraction motion, the techniques and apparatus discussed herein may also be used for maintaining the position of a focus of an optical component relative to another component (e.g., in the context of external disturbances).

In an embodiment, to provide the control described herein, there may be little, or no, impact on mechanical hardware, there may be limited impact on optical hardware, and there may be limited impact on motion control software through extension of a set point generator and applicable signal processing.

As described above, in an embodiment, there were provided various techniques to provide position control in respect of the focus position by a technique based on one or more specific signals. The techniques have particular applicability in an optical metrology or inspection apparatus such as a scatterometer, an alignment sensor (which determines alignment using one or more alignment marks), an encoder or interferometer (which enables position measurement), and/or a height or level sensor (which enables measuring of the position of a surface), but can be applied in other applications of SILs or in other applications where an object is positioned and/or maintained very close to another object (e.g., in the below 400 nm range). The technique need not be applied exclusively, and could be applied in combination with one or more other techniques, including one or more techniques discussed in the cited documents.

While the various embodiments herein primarily describe position control between a SIL and an objective, the disclosed methods and apparatus may be used to control the position of any optical component relative to another optical component.

Reference to the gap is not intended to imply that a medium between SIL 60 and target 30 must be, e.g., air, or even that it must be gaseous. The medium within the gap in any particular implementation may be a vacuum or partial vacuum, any gaseous or liquid medium, whose refractive index meets the requirements of the optical functions of the apparatus.

Detectors described herein may measure the intensity of radiation at a single wavelength (or narrow wavelength range), the intensity separately at multiple wavelengths or the intensity integrated over a wavelength range. Detectors described herein may separately measure the intensity of transverse magnetic- and transverse electric-polarized radiation and/or the phase difference between the transverse magnetic- and transverse electric-polarized radiation. Detectors described herein may detect polarized radiation passing via a polarizer and so provide polarization sensitive detection without, for example, necessarily measuring polarization.

The algorithms described in this document may be implemented via coding of a suitable software program to be performed by, e.g., processor system PU or its equivalent in the form of a dedicated microprocessor or the like.

Any controllers or control systems described herein may each or in combination be operable when the one or more computer programs are read by one or more computer processors located within at least one component of the lithographic apparatus. The controllers or control systems may each or in combination have any suitable configuration for receiving, processing, and sending signals. One or more processors are configured to communicate with the at least one of the controllers or control systems. For example, each controller or control system may include one or more processors for executing the computer programs that include machine-readable instructions for the methods described above. The controllers or control systems may include a data storage medium for storing such computer programs, and/or hardware to receive such medium. So the controller(s) or control system(s) may operate according the machine readable instructions of one or more computer programs.

Further embodiments according to the invention are provided in below numbered clauses:

1. A method, comprising:
    providing incident radiation of a first polarization state by an optical component into an interface of an object with an external environment, wherein a surface is provided adjacent the interface and separated by a gap from the interface;
    detecting, from incident radiation reflected from the interface and from the surface, radiation of a second different polarization state arising from the reflection of incident radiation of the first polarization at the interface as distinct from the radiation of the first polarization state in the reflected radiation; and
    producing a position signal representative of a position of the object and/or the component based on the detected radiation.
2. The method of clause 1, further comprising filtering the radiation of the second different polarization state from the reflected radiation.
3. The method of clause 2, wherein the filtering comprises passing the reflected radiation via a polarizer.
4. The method of clause 3, wherein the polarizer substantially only propagates radiation in the second polarization state.
5. The method of any of clauses 2-4, wherein the filtering comprises removing a central portion of the reflected radiation such that the detected radiation is radiation outside the central portion.
6. The method of clause 1, comprising increasing a proportion of the radiation of the second polarization state in the reflected radiation or reducing a proportion of the radiation of the first polarization state in the reflected radiation.
7. The method of any of clauses 1-6, wherein the radiation of the first polarization state comprises radiation linearly polarized in a first direction and the radiation of the second polarization state comprises radiation linearly polarized in a second orthogonal direction.
8. The method of any of clause 1-6, wherein the radiation of the first polarization state comprises circularly polarized radiation.
9. The method of any of clauses 1-8, wherein the reflected radiation reflects due to total internal reflection at the interface.
10. The method of any of clauses 1-9, further comprising focusing, by the optical component, the radiation in the first polarization state at the interface.
11. The method of any of clauses 1-10, wherein the position signal is representative of a relative position between the focus of the optical component and the object.
12. The method of any of clauses 1-11, further comprising controlling a relative position between the optical component and the object based on the position signal to provide or maintain a focus of the optical component at or near the interface.
13. The method of clause 12, wherein the controlling comprises closed loop control to actively damp the relative position and/or suppress an external disturbance acting on the optical component and/or object.

14. The method of any of clauses 1-13, further comprising controlling a relative position between the optical component and the object during a relative movement between the (i) the optical component and the object and (ii) the surface adjacent the interface.

15. A method, comprising:
focusing radiation by an optical component into an object toward an interface of the object with an external environment;
reflecting, at the interface, focused radiation by total internal reflection;
detecting reflected radiation; and
producing a position signal representative of the relative position between the focus of the optical component and the object based on the detected reflected radiation.

16. The method of clause 15, further comprising controlling a relative position between the optical component and the object based on the position signal to provide or maintain the focus of the optical component at or near the interface.

17. The method of clause 16, wherein the controlling comprises closed loop control to actively damp the relative position and/or suppress an external disturbance acting on the optical component and/or object.

18. The method of any of clauses 15-17, further comprising controlling a relative position between the optical component and the object during a relative movement between the (i) the optical component and/or the object and (ii) a surface adjacent the interface.

19. The method of any of clauses 15-18, wherein the focused radiation comprises polarized radiation.

20. A method, comprising:
providing, by an optical component, radiation of a first polarization state into an object toward an interface of the object with an external environment;
reflecting radiation from the interface, the reflected radiation comprising radiation of a second polarization state orthogonal to the first polarization state arising from the reflection of the radiation of the first polarization state at the interface;
processing the reflected radiation to produced processed radiation having substantially only radiation of the second polarization state or having a higher proportion of the radiation of the second polarization state than the first polarization state relative to the reflected radiation; and
detecting the processed radiation and producing a position signal representative of the position of the object and/or the component based on the detected processed radiation.

21. The method of clause 20, wherein the first polarization state is linear polarization in a first direction and the second polarization state is linear polarization in a second orthogonal direction.

22. The method of clause 20 or clause 21, wherein processing the reflected radiation comprises using a polarizer that substantially only propagates radiation of the second polarization state.

23. The method of any of clauses 20-22, wherein the reflected radiation reflects due to total internal reflection at the interface.

24. The method of any of clauses 20-23, further comprising focusing, by the optical component, the radiation of the first polarization state at the interface.

25. The method of any of clauses 20-24, wherein the position signal is representative of a relative position between the focus of the optical component and the object.

26. The method of any of clauses 20-25, further comprising controlling a relative position between the optical component and the object based on the position signal to provide or maintain a focus of the optical component at or near the interface.

27. The method of clause 26, wherein the controlling comprises closed loop control to actively damp the relative position and/or suppress an external disturbance acting on the optical component and/or object.

28. The method of any of clauses 20-27, further comprising controlling a relative position between the optical component and the object during a relative movement between the (i) the optical component and/or the object and (ii) a surface adjacent the interface.

29. A method, comprising:
providing incident radiation by an optical component into an object toward an interface of the object with an external environment, wherein a surface is provided adjacent the interface and separated by a gap from the interface;
processing reflected radiation arising from the reflection of the incident radiation at the interface and at the surface to reduce a proportion of radiation reflected from the surface in the reflected radiation; and
producing a position signal representative of a position of the object and/or the component based on the processed radiation.

30. The method of clause 29, wherein the incident radiation comprises linearly polarized in a first direction.

31. The method of clause 30, wherein the processing comprises reducing an amount of radiation linearly polarized in the first direction in the reflected radiation.

32. The method of clause 31, wherein the processing comprises processing the reflected radiation using a polarizer that substantially only propagates radiation that is linearly polarized in a second direction different from the first direction.

33. The method of clause 32, wherein producing the position signal comprises detecting radiation linearly polarized in the second direction and producing the position signal representative based on the detected radiation linearly polarized in the second direction.

34. The method of any of clauses 29-33, wherein the reflected radiation from the interface reflects due to total internal reflection at the interface.

35. The method of any of clauses 29-34, further comprising focusing, by the optical component, the radiation at the interface.

36. The method of any of clauses 29-35, wherein the position signal is representative of a relative position between the focus of the optical component and the object.

37. The method of any of clauses 29-36, further comprising controlling a relative position between the optical component and the object based on the position signal to provide or maintain a focus of the optical component at or near the interface.

38. The method of clause 37, wherein the controlling comprises closed loop control to actively damp the relative position and/or suppress an external disturbance acting on the optical component and/or object.

39. The method of any of clauses 29-38, further comprising controlling a relative position between the optical component and the object during a relative movement between the (i) the optical component and/or the object and (ii) the surface.

40. A method, comprising:
   providing radiation that is circularly polarized by an optical component into an object toward an interface of the object with an external environment; and
   producing a position signal representative of a position of the object and/or objective based substantially only on radiation reflected from the interface arising from radiation incident at the interface at angles greater than a critical angle associated with the interface.
41. The method of clause 40, further comprising blocking radiation reflected from the interface arising from radiation incident at the interface at angles less than or equal to the critical angle associated with the interface.
42. The method of clause 41, wherein the blocking comprises using a mask comprising an aperture spaced apart from the intersection of the optical axis of the reflected radiation with the mask.
43. The method of clause 40 or clause 41, comprising detecting radiation reflected from the interface that is not blocked and producing the position signal representative based on the detected reflected radiation.
44. The method of any of clauses 40-43, wherein radiation of a different polarization state than the circularly polarized radiation arises from the reflection of the incident radiation at the interface and further comprising filtering the radiation of the different polarization state from the reflected radiation.
45. The method of clause 44, wherein the filtering comprises passing the reflected radiation via a polarizer.
46. The method of any of clauses 40-45, further comprising focusing, by the optical component, the radiation at the interface.
47. The method of any of clauses 40-46, wherein the position signal is representative of a relative position between the focus of the optical component and the object.
48. The method of any of clauses 40-47, further comprising controlling a relative position between the optical component and the object based on the position signal to provide or maintain a focus of the optical component at or near the interface.
49. The method of clause 48, wherein the controlling comprises closed loop control to actively damp the relative position and/or suppress an external disturbance acting on the optical component and/or object.
50. The method of any of clauses 40-49, further comprising controlling a relative position between the optical component and the object during a relative movement between the (i) the optical component and/or the object and (ii) a surface adjacent the interface.
51. The method of any of clauses 1-50, wherein the object comprises a solid immersion lens.
52. The method of any of clauses 1-51, wherein the optical component comprises an objective.
53. The method of any of clauses 1-52, further comprising positioning the object within 1 nm to 400 nm of a surface.
54. A method of manufacturing devices wherein a device pattern is applied to a series of substrates using a lithographic process, the method including inspecting at least a target formed as part of or beside the device pattern on at least one of the substrates using the method of any of clauses 1-53, and controlling the lithographic process for later substrates in accordance with the result of the method.
55. A non-transitory computer program product comprising machine-readable instructions for causing a processor to cause performance of the method of any of clauses 1-54.
56. A system comprising:
   an inspection apparatus configured to provide a beam on a measurement target on a substrate and to detect radiation redirected by the target to determine a parameter of a lithographic process; and
   the non-transitory computer program product of clause 55.
57. The system of clause 56, further comprising a lithographic apparatus comprising a support structure configured to hold a patterning device to modulate a radiation beam and a projection optical system arranged to project the modulated onto a radiation-sensitive substrate.

Although specific reference may have been made in this text to the use of embodiments of the invention in the context of metrology or inspection apparatus used to inspect or measure items in association with, e.g., optical lithography, it will be appreciated that the methods and apparatus described herein may be used in other applications, for example imprint lithography, the use or manufacture of integrated optical systems, the use or manufacture of guidance and detection patterns for magnetic domain memories, the use or manufacture of flat-panel displays, the use or manufacture of liquid-crystal displays (LCDs), the use or manufacture of thin film magnetic heads, etc. The substrate referred to herein may be processed, before or after exposure, in for example a track (a tool that typically applies a layer of resist to a substrate and develops the exposed resist), a metrology tool and/or an inspection tool. Where applicable, the disclosure herein may be applied to such and other substrate processing tools. Further, the substrate may be processed more than once, for example in order to create a multi-layer IC, so that the term substrate used herein may also refer to a substrate that already contains multiple processed or unprocessed layers.

The terms "radiation" and "beam" used herein encompass all types of electromagnetic radiation, including ultraviolet (UV) radiation (e.g. having a wavelength of less than about 400 nm and greater than about 20 nm, or about 365, 355, 248, 193, 157 or 126 nm).

The term "lens", where the context allows, may refer to any one or combination of various types of optical components, including refractive, reflective, magnetic, electromagnetic and electrostatic optical components.

While specific embodiments of the invention have been described above, it will be appreciated that the invention may be practiced otherwise than as described. For example, an embodiment of the invention may take the form of a computer program containing one or more sequences of machine-readable instructions describing a method as disclosed herein, or a non-transitory data storage medium (e.g. semiconductor memory, magnetic or optical disk, etc.) or a transitory medium having such a computer program therein. Further, the machine readable instruction may be embodied in two or more computer programs. The two or more computer programs may be stored on one or more different data storage media.

The descriptions above are intended to be illustrative, not limiting. Thus, it will be apparent to one skilled in the art that modifications may be made to the invention as described without departing from the scope of the claims set out below.

What is claimed is:
1. A method, comprising:
   providing incident radiation of a first polarization state by an optical component into an interface of an object with an external environment, wherein a surface is provided adjacent the interface and separated by a gap from the interface;

detecting, from incident radiation reflected from the interface and from the surface, radiation of a second different polarization state arising from the reflection of incident radiation of the first polarization at the interface as distinct from the radiation of the first polarization state in the reflected radiation; and producing a position signal representative of a relative position between a focus of the optical component and the object based on detected reflected radiation that excludes reflected radiation arising from radiation incident at the interface at angles less than or equal to a critical angle associated with the interface.

2. The method of claim 1, further comprising filtering the radiation of the second different polarization state from the reflected radiation using a polarizer.

3. The method of claim 2, wherein the polarizer substantially only propagates radiation in the second polarization state.

4. The method of claim 2, wherein the filtering comprises removing a central portion of the reflected radiation such that the detected radiation is radiation outside the central portion.

5. The method of claim 1, wherein the radiation of the first polarization state comprises radiation polarized in a first direction and the radiation of the second polarization state comprises radiation polarized in a second orthogonal direction.

6. A method of manufacturing devices wherein a device pattern is applied to a series of substrates using a lithographic process, the method including inspecting at least a target formed as part of or beside the device pattern on at least one of the substrates using the method of claim 1, and controlling the lithographic process for one or more later substrates in accordance with the result of the method.

7. The method of claim 1, wherein the radiation of the first polarization state comprises radiation linearly polarized in a first direction and the radiation of the second polarization state comprises radiation linearly polarized in a second orthogonal direction.

8. The method of claim 1, wherein the object comprises a solid immersion lens.

9. The method of claim 1, further comprising blocking radiation reflected from the interface arising from radiation incident at the interface at angles less than or equal to a critical angle associated with the interface.

10. A method, comprising:
focusing radiation by an optical component into an object toward an interface of the object with an external environment;
reflecting, at the interface, focused radiation by total internal reflection;
detecting reflected radiation; and
producing a position signal representative of a relative position between a focus of the optical component and the object based on the detected reflected radiation that excludes reflected radiation arising from radiation incident at the interface at angles less than or equal to a critical angle associated with the interface.

11. The method of claim 10, further comprising controlling a relative position between the optical component and the object based on the position signal to provide or maintain the focus of the optical component at or near the interface.

12. The method of claim 11, wherein the controlling comprises closed loop control to actively damp the relative position and/or suppress an external disturbance acting on the optical component and/or object.

13. The method of claim 11, further comprising controlling a relative position between the optical component and the object during a relative movement between the (i) the optical component and/or the object and (ii) a surface adjacent the interface.

14. The method of claim 10, further comprising blocking radiation reflected from the interface arising from radiation incident at the interface at angles less than or equal to a critical angle associated with the interface.

15. The method of claim 14, wherein the blocking comprises using a mask comprising an aperture spaced apart from the intersection of the optical axis of the reflected radiation with the mask.

16. The method of claim 14, comprising detecting radiation reflected from the interface that is not blocked and producing the position signal representative based on the detected reflected radiation.

17. The method of claim 10, wherein the object comprises a solid immersion lens.

18. A non-transitory computer program product comprising machine-readable instructions, that when executed, cause a processor system to cause performance in an apparatus of at least:
provision of incident radiation of a first polarization state by an optical component into an interface of an object with an external environment, wherein a surface is provided adjacent the interface and separated by a gap from the interface;
detection, from incident radiation reflected from the interface and from the surface, radiation of a second different polarization state arising from the reflection of incident radiation of the first polarization at the interface as distinct from the radiation of the first polarization state in the reflected radiation; and
production of a position signal representative of a relative position between a focus of the optical component and the object based on detected reflected radiation that excludes reflected radiation arising from radiation incident at the interface at angles less than or equal to a critical angle associated with the interface.

19. A system comprising:
an inspection apparatus configured to provide a beam on a measurement target on a substrate and to detect radiation redirected by the target to determine a parameter of a lithographic process; and
the non-transitory computer program product of claim 18.

20. The system of claim 19, further comprising a lithographic apparatus comprising a support structure configured to hold a patterning device to modulate a radiation beam and a projection optical system arranged to project the modulated onto a radiation-sensitive substrate.

* * * * *